(12) United States Patent
Kim et al.

(10) Patent No.: US 9,176,205 B2
(45) Date of Patent: Nov. 3, 2015

(54) MICROFLUIDIC CHIP FOR SUSCEPTIBILITY OF SUPERPARAMAGNETIC NANOPARTICLES OF BEAD AND DROPLET TYPES AND MEASURING METHOD FOR SUSCEPTIBILITY USING THE SAME

(71) Applicant: THE INDUSTRY & ACADEMIC COOPERATION IN CHUNGNAM NATIONAL UNIVERSITY (IAC), Daejeon (KR)

(72) Inventors: CheolGi Kim, Seoul (KR); IlGyo Jeong, Daejeon (KR); Young-Jae Eu, Daejeon (KR); KunWoo Kim, Daejeon (KR); XingHao Hu, Daejeon (KR); Brajalal Sinha, Daejeon (KR)

(73) Assignee: The Industry & Academic Cooperation in Chungnam National University (IAC), Daejeon (KR)

( * ) Notice: Subject to any disclaimer, the term of this patent is extended or adjusted under 35 U.S.C. 154(b) by 237 days.

(21) Appl. No.: 13/865,529

(22) Filed: Apr. 18, 2013

(65) Prior Publication Data
US 2013/0285648 A1    Oct. 31, 2013

(30) Foreign Application Priority Data

Apr. 19, 2012    (KR) .................. 10-2012-0040982
Apr. 18, 2013    (KR) .................. 10-2013-0042714

(51) Int. Cl.
*G01R 33/12* (2006.01)
*G01R 33/07* (2006.01)
*G01N 27/74* (2006.01)

(52) U.S. Cl.
CPC .......... *G01R 33/1238* (2013.01); *G01N 27/745* (2013.01); *G01R 33/07* (2013.01); *G01R 33/1269* (2013.01)

(58) Field of Classification Search
CPC ............... G01R 33/1238; G01R 33/07; G01R 33/1269; G01N 27/745
USPC .......................................... 324/201, 204, 251
See application file for complete search history.

(56) References Cited

U.S. PATENT DOCUMENTS

| 4,359,752 | A  | * | 11/1982 | Nakagawa et al. | 347/53 |
| 2010/0124572 | A1 | * | 5/2010 | Wen et al. | 424/490 |
| 2010/0233822 | A1 | * | 9/2010 | Prins et al. | 436/164 |

OTHER PUBLICATIONS

G. Mihajlovic, K. Aledealat, P. Xiong, S.v. Molnar, M. Field, G. J. Sullivan, Appl. Phys. Lett. 91 (2007) 172518.
P. P. Freitas, R. Ferreria, S. Cardoso and F. Cardoso, J. Phys.: Condens. Matter 19, 165221 (2007).
D. L. Graham, H. A. Ferreira and P. P. Freitas, Trends Biotechnol. 22, 455 (2004).
B. Srinivasan, Y. Li, Y. Jing, Y. Xu, X. Yao, C. Xing and J. Wang, Angew. Chem. Int. Ed. 48, 2764 (2009).

(Continued)

*Primary Examiner* — Tung X Nguyen
*Assistant Examiner* — Robert P Alejnikov, Jr.
(74) *Attorney, Agent, or Firm* — Lucas & Mercanti, LLP

(57) ABSTRACT

The present invention relates to a microfluidic chip for measuring the magnetic susceptibility of a superparamagnetic nanoparticle droplet and a method for measuring magnetic susceptibility using the same. According to the invention, the magnetic susceptibility of a superparamagnetic nanoparticle can be continuously and accurately measured in a flowing fluid using a microfluidic chip including microfluidic channels.

14 Claims, 18 Drawing Sheets

(56) References Cited

OTHER PUBLICATIONS

R. S. Gaster, L. Xu, S. Han, R. J. Wilson, D. A. Hall, S. J. Osterfeld, H. Yu and S. X. Wang, Nature Nanotech. 6, 314 (2011).

R. S. Gaster, D. A. Hall, C. H. Nielsen, S. J. Osterfeld, H. Yu, K. E. Mach, R. J. Wilson, B. Murmann, J. C. Liao, S. S. Gambhir and S. X. Wang, Nature Med. 15, 1327 (2009).

Y. Li, B. Srinviasan, Y. Jing, X. Yao, M. A. Hugger, J. Wang and C. Xing, J. Am. Chem. Soc. 132, 4388 (2010).

P. Besse, G. Boero, M. Demierre, V. Pott and R. Popovic, Appl. Phys. Lett. 80, 4199 (2002).

W. Shen, X. Liu, D. Mazumdar and G. Xiao, Appl. Phys. Lett. 86, 253901 (2005).

L. Ejsing, M. F. Hansen, A. K. Menon, H. A. Ferreira, D. L. Graham and P. P. Freitas, Appl. Phys. Lett. 84, 4729 (2004).

U.S. Appl. No. 61/126,004, priority documents for PCT/US00/07829.

* cited by examiner (a)

(b)

(c)

MICROFLUIDIC CHIP FOR SUSCEPTIBILITY OF SUPERPARAMAGNETIC NANOPARTICLES OF BEAD AND DROPLET TYPES AND MEASURING METHOD FOR SUSCEPTIBILITY USING THE SAME

CROSS-REFERENCE TO RELATED APPLICATIONS

This application claims priority from Korean Patent Application No. 10-2012-0040982, filed on Apr. 19, 2012, and Korean Patent Application No. 10-2013-0042714, filed on Apr. 18 2013, in the Korean Intellectual Property Office, the disclosure of which is incorporated herein by reference in its entirety.

BACKGROUND OF THE INVENTION

1. Field of the Invention

The present invention relates to a microfluidic chip for measuring the magnetic susceptibility of a superparamagnetic nanoparticle bead and droplet and a method for measuring magnetic susceptibility using the same.

2. Description of the Related Art

Superparamagnetic nanoparticle beads have been used in magnetic biosensors to detect the biomaterials to be analyzed. The superparamagnetic nanoparticle beads are materials which show magnetic properties upon the application of an external magnetic field, but lose the magnetic properties when the magnetic field is removed. Using the properties of such superparamagnetic nanoparticle beads, magnetic biosensors can detect biomaterials in liquid media, classify the type of biomaterial, and provide information on the position of the biomaterials. Thus, the magnetic properties of the superparamagnetic nanoparticle beads play an important role in determining the abilities of the biosensors, such as the ability to diagnose and resolve the biomaterial to be analyzed, and the ability to transport biomaterials.

The superparamagnetic nanoparticle beads are characterized in that they are magnetized by an externally applied magnetic field to produce a stray magnetic field ($H_{stray}$). For this reason, when the superparamagnetic nanoparticle beads are present around a sensor, the total effective magnetic field ($H_{eff}$) in the sensor can be determined by the sum of vectors of an externally applied magnetic field ($H_{app}$) and an induced magnetic field generated from the superparamagnetic nanoparticle beads magnetized by the externally applied magnetic field ($H_{app}$).

Thus, using the characteristic in that a magnetic field in a magnetic biosensor changes depending on the presence or absence of superparamagnetic nanoparticle beads, the magnetic biosensor can sense magnetic resistance caused by the change of the magnetic field to detect the biomaterial to be analyzed.

The superparamagnetic nanoparticle beads are generally in a form in which superparamagnetic nanoparticles such as iron oxide ($Fe_3O_4$) or γ-iron oxide (γ-$Fe_2O_3$) nanoparticles are dispersed on spherical polymer matrices, and have a very small volume, and thus magnetic signals generated therefrom are also very fine. Accordingly, studies on the effective detection of magnetic signals from the superparamagnetic nanoparticle beads have been conducted.

Conventional methods for measuring the magnetic properties of superparamagnetic nanoparticle beads, such as their magnetic susceptibility, magnetic field dependence and saturation magnetization, include a method employing a superconducting quantum interference device (SQUID), a method employing a vibrating sample magnetometer, and the like.

PCT Patent Application No. PCT/US00/007829 discloses a method for measuring the magnetic susceptibility of a magnetic material using a superconducting quantum interference device. Specifically, PCT Patent Application No. PCT/US00/007829 discloses a method for measuring the magnetic susceptibility of a magnetic material using an apparatus comprising a superconducting material disposed on a flexible metallic substrate, a permanent magnet for applying a magnetic field, a superconducting quantum interference device, and a magnetic flux transformer. The above method has disadvantages in that, because the superconducting quantum interference device is used, a large number of control elements for performing the process are used, the method is not suitable for use for point-of-care testing due to elements that are used at very low temperatures, and high costs are incurred.

In addition, the method for measuring the magnetic susceptibility of superparamagnetic nanoparticle beads using a vibrating sample magnetometer comprises forming a strong magnetic field in a system to magnetize a sample, and measuring the susceptibility of the sample while vibrating the sample upward and downward. This method is not suitable for use for point-of-care testing, because it consumes a large amount of power.

In the above measurement methods, the magnetic susceptibility of a sample is measured using a nanoparticle bead cluster, which has a volume of about 100 μg and comprises 10,000 or more nanoparticles. Thus, in the above methods, the magnetic susceptibility of the nanoparticle bead cluster is measured, and the magnetic susceptibility of the nanoparticles is deduced from the results of the measurement. For this reason, there are limitations in the quantitative measurement or high-sensitivity measurement of each nanoparticle bead.

Meanwhile, with respect to methods for measuring the magnetic properties of a sample using superparamagnetic nanoparticle beads, studies as described below have been reported. For example, the literature [G. Mihajlovic, K. Aledealat, P. Xiong, S. v. Molnar, M. Field, G. J. Sullivan, "Magnetic characterization of a single superparamagnetic bead by phase-sensitive micro-Hall magnetometry", Appl. Phys. Lett. 91 (2007) 172518] discloses a method of measuring the magnetic susceptibility of a superparamagnetic nanoparticle bead having a diameter of 1.2 μm, in which the magnetic susceptibility of the superparamagnetic nanoparticle bead is measured using a micro-sized semiconductor Hall sensor, in which the sensor element does not produce an induced magnetic field. Specifically, in this method, the magnetic susceptibility of the nanoparticle bead in a region to which a low magnetic field is applied is formulated by the Langevin function, and its value is obtained by fitting a curve to the Hall sensor output voltage versus an externally applied magnetic field, with the fitting parameters being the distribution median and the constituent magnetic nanoparticles. This method is characterized in that the curve of the Hall sensor output voltage versus the externally applied magnetic field is well fitted, because a single bead sample is used, unlike the method that uses the nanoparticle bead cluster as a sample.

In addition, magnetic sensors are used in various fields to sense magnetic fields, store data, sense the position of proximity switches, sense speed, and sense electric currents.

Magnetoresistive sensors have high sensitivity even in a very low magnetic field at room temperature and can be used to sense biomolecules (P. P. Freitas, R. Ferreria, S. Cardoso and F. Cardoso, "Magnetoresistive sensors", J. Phys.: Condens. Matter 19, 165221 (2007), D. L. Graham, H. A. Ferreira and P. P. Freitas, "Magnetoresistive-based biosensors and biochips", Trends Biotechnol. 22, 455 (2004), B. Srinivasan, Y. Li, Y. Jing, Y. Xu, X. Yao, C. Xing and J. Wang, "A detection system based on giant magnetoresistive sensors and high-moment magnetic nanoparticles demonstrates zeptomole sensitivity: potential for personalized medicine" Angew. Chem. Int. Ed. 48, 2764 (2009), R. S. Gaster, L. Xu, S. Han, R. J. Wilson, D. A. Hall, S. J. Osterfeld, H. Yu and S. X. Wang, "Quantification of Protein Interactions and Solution Transport Using High-Density GMR Sensor Arrays" Nature Nanotech. 6, 314 (2011), R. S. Gaster, D. A. Hall, C. H. Nielsen, S. J. Osterfeld, H. Yu, K. E. Mach, R. J. Wilson, B. Murmann, J. C. Liao, S. S. Gambhir and S. X. Wang, "Matrix-insensitive protein assays push the limits of biosensors in medicine", Nature Med. 15, 1327 (2009), Y. Li, B. Srinviasan, Y. Jing, X. Yao, M. A. Hugger, J. Wang and C. Xing, "Nanomagnetic competition assay for low-abundance protein biomarker quantification in unprocessed human sera", J. Am. Chem. Soc. 132, 4388 (2010)). When a protein, an antibody or a nucleic acid is attached to nanoparticles or nanoparticle beads which are immobilized onto the surface of magnetic sensors, it can assist in finding molecules. Many types of magnetic nanoparticles perform roles such as biological labels in colloidal suspensions and can be integrated according to functions and application fields (D. L. Graham, H. A. Ferreira and P. P. Freitas, "Magnetoresistive-based biosensors and biochips", Trends Biotechnol. 22, 455 (2004)). Superparamagnetic nanoparticles having a size of 10 nm have no remnant magnetism and show good dispersibility. Magnetic fluids are stable colloidal suspensions of magnetic nanoparticles.

Most initial studies were focused on improving the detection limit of magnetic sensors in magnetic fields. Many kinds of sensors have been developed, including giant magnetoresistive (GMR) sensors, anisotropic magnetoresistive (AMR) sensors, semiconductor Hall sensors, planar Hall resistive (PHR) sensors, and magnetic tunnel junctions (MTJs) (D. L. Graham, H. A. Ferreira and P. P. Freitas, "Magnetoresistive-based biosensors and biochips", Trends Biotechnol. 22, 455 (2004)). These sensors can sense even single magnetic nanoparticle beads and include semiconductor Hall sensors (P. Besse, G. Boero, M. Demierre, V. Pott and R. Popovic, "Detection of a single magnetic microbead using a miniaturized silicon Hall sensor", Appl. Phys. Lett. 80, 4199 (2002)), magnetic tunnel junctions (MTJs) (W. Shen, X. Liu, D. Mazumdar and G. Xiao, "In situ detection of single micron-sized magnetic beads using magnetic tunnel junction sensors", Appl. Phys. Lett. 86, 253901 (2005)), and planar Hall effect sensors (L. Ejsing, M. F. Hansen, A. K. Menon, H. A. Ferreira, D. L. Graham and P. P. Freitas, "Planar Hall effect sensor for magnetic micro- and nanobead detection", Appl. Phys. Lett. 84, 4729 (2004)). Measurement systems have developed toward the use of a lock-in amplifier to increase signal-to-noise ratio.

For application to biosensors, systems comprising a magnetic sensor integrated with a microfluidic system (P. Besse, G. Boero, M. Demierre, V. Pott and R. Popovic, "Detection of a single magnetic microbead using a miniaturized silicon Hall sensor", Appl. Phys. Lett. 80, 4199 (2002)) have been developed. When magnetic nanoparticle beads and nanoparticles are exposed on the sensor, a magnetic signal is measured as an electrical signal. The sensor integrated with the microfluidic system can sense the nanoparticles and nanobeads that flow.

When a valve, a pump and a mixer together with a magnetic sensor are added to a microfluidic system, an automated and complex analysis system can be developed.

Magnetic fluids have been widely used in experiments on the performance of magnetic materials (L. Ejsing, M. F. Hansen, A. K. Menon, H. A. Ferreira, D. L. Graham and P. P. Freitas, "Planar Hall effect sensor for magnetic micro- and nanobead detection", Appl. Phys. Lett. 84, 4729 (2004)). Most reported magnetic fluid signals had problems in that slowly flowing signals were sensed, the sensed signals were weak, and the time resolution of the signals was also poor.

Accordingly, the present inventor has developed a microfluidic chip including a planar Hall resistive sensor and has found a method for measuring the magnetic susceptibility of a superparamagnetic nanoparticle bead and droplet in a flowing magnetic fluid using the microfluidic chip, thereby completing the present invention.

SUMMARY OF THE INVENTION

It is an object of the present invention to provide a microfluidic chip comprising a microfluidic channel, which is used for the measurement of the magnetic susceptibility of a superparamagnetic nanoparticle bead and droplet in a magnetic fluid.

Another object of the present invention is to provide a method for measuring magnetic susceptibility using the above microfluidic chip.

Still another object of the present invention is to provide a planar Hall resistive sensor for measuring magnetic susceptibility, which has increased accuracy as a result of controlling the arm length.

Yet another object of the present invention is to provide a method for measuring the magnetic susceptibility of a superparamagnetic nanoparticle bead and droplet using the above planar Hall resistive sensor for measuring magnetic susceptibility.

To achieve the above objects, the present invention provides a microfluidic chip for measuring the magnetic susceptibility of a superparamagnetic nanoparticle bead, the microfluidic chip comprising: a planar Hall resistive sensor comprising an active junction area for sensing the superparamagnetic nanoparticle bead and droplet, which protrudes from an underlying substrate and in which a first arm having current electrodes at both ends and a second arm having voltage electrodes at both ends cross each other, wherein the first arm has a controlled length; and microfluidic channels crossing over the active junction area of the planar Hall resistive sensor.

The present invention also provides a method for measuring the magnetic susceptibility of a superparamagnetic nanoparticle bead, the method comprising the steps of:

(1) injecting a continuous phase fluid and a magnetic fluid into a continuous phase fluid-moving microfluidic channel and a magnetic fluid-moving microfluidic channel, respectively, in a microfluidic chip;

(2) allowing the continuous phase fluid and the magnetic fluid, injected in step (1), to meet each other to form a superparamagnetic nanoparticle bead droplet; and (3) measuring the magnetic susceptibility of a superparamagnetic nanoparticle bead present in the droplet when the superparamagnetic nanoparticle bead droplet formed in step (2) passes over the active junction area of a planar Hall resistive sensor.

The present invention also provides a planar Hall resistive sensor comprising an active junction area for sensing the superparamagnetic nanoparticle bead, which protrudes from an underlying substrate and in which a first arm having current electrodes at both ends and a second arm having voltage electrodes at both ends cross each other, wherein the first arm has a controlled length. The present invention also provides a method for measuring the magnetic susceptibility of a superparamagnetic nanoparticle bead.

According to the present invention, the planar Hall resistive sensor and the microfluidic channels are embodied on a single chip. Thus, the magnetic susceptibility of a superparamagnetic nanoparticle bead in a flowing fluid can be continuously measured, and the chip can be miniaturized so that the magnetic susceptibility can be measured with a high accuracy even when a magnetic fluid is used in a small amount (on the order of picoliters).

BRIEF DESCRIPTION OF THE DRAWINGS

FIG. 5 shows processes in which a superparamagnetic nanoparticle bead droplet is formed over time in the intersection of the T-shaped microfluidic channel when pressure applied to the second inlet port 15 is the lowest (FIG. 5(a)), pressure applied to the second inlet port 15 is intermediate (FIG. 5(b)) and pressure applied to the second inlet port 15 is the highest (FIG. 5(c));

DETAILED DESCRIPTION OF THE INVENTION

Figure 1:
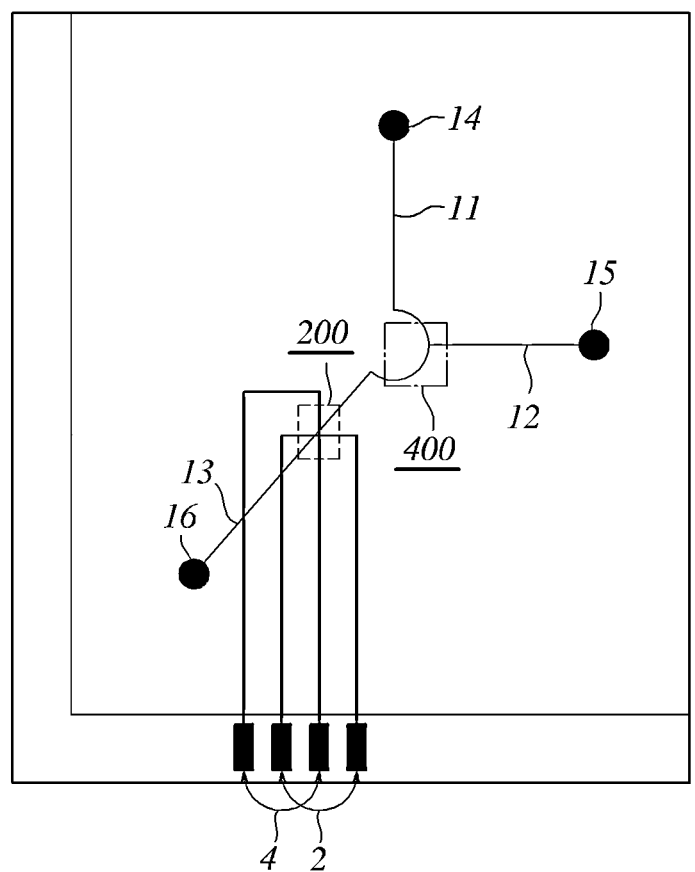
FIG. 1 is a schematic view of a microfluidic chip comprising microfluidic channels 11, 12 and 13 and a planar Hall resistive sensor 200 according to an embodiment of the present invention.
Figure 2:
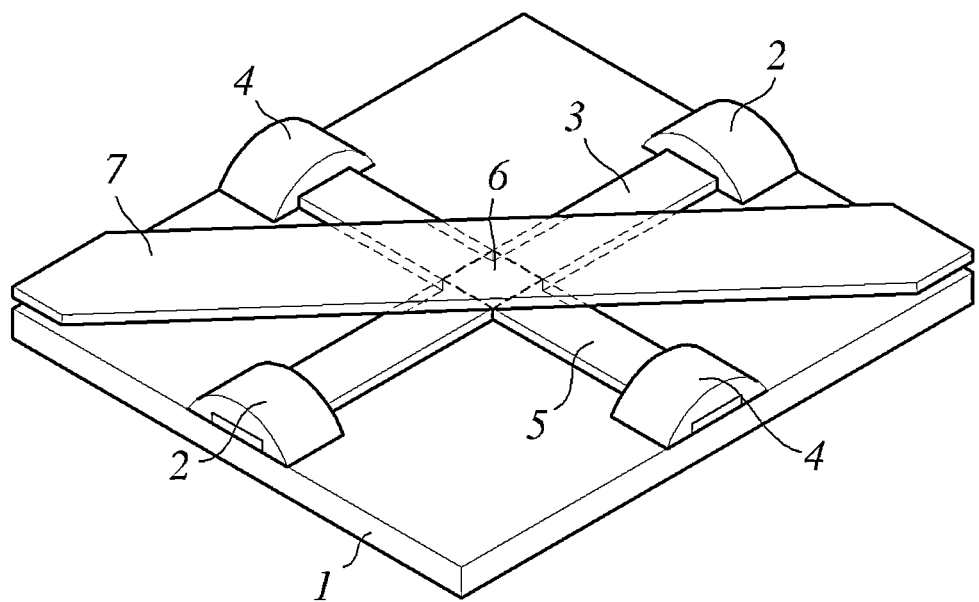
FIG. 2 is an enlarged view of the planar Hall resistive sensor 200 in the microfluidic chip of FIG. 1 according to an embodiment of the present invention.

The present invention provides a microfluidic chip capable of measuring a superparamagnetic nanoparticle bead and droplet.

Hereinafter, the present invention will be described in detail.

The inventive microfluidic chip for measuring the magnetic susceptibility of a superparamagnetic nanoparticle bead comprises: a planar Hall resistive sensor 200 comprising an active junction area 6 for sensing the superparamagnetic nanoparticle bead and droplet, which protrudes from an underlying substrate 1 and in which a first arm 3 having current electrodes 2 at both ends and a second arm 5 having voltage electrodes 4 at both ends cross each other, wherein the first arm 3 has a controlled length; and microfluidic channels 11, 12 and 13 crossing over the active junction area of the planar Hall resistive sensor.

Specifically, the underlying substrate 1 is an element on which the stack structure of the arms and the sensor are based. It is placed in the lowest portion of the microfluidic chip and has thereon the first arm and second arm, which form the two axes of the planar Hall resistive sensor present in the microfluidic chip. The first arm has the current electrodes 2 at both ends, and the second arm has the voltage electrodes 4 at both ends. Thus, an electrical signal (difference in voltage) converted from a magnetic signal is sensed by the Hall effect. In other words, an external magnetic field is applied in a state in which an electric current flows to the current electrodes 2, the voltage difference sensed by the sensor due to the magnetic property of the superparamagnetic nanoparticle bead is measured by the voltage electrodes 4.

Further, the portion in which the first arm and the second arm cross each other is a portion serving as a sensor required for actual measurement and is referred to as the active junction area.

Furthermore, the microfluidic channels extend across over the active junction area so that a magnetic fluid and a continuous phase continuously pass through the center of the active junction area.

In addition, in the microfluidic chip according to the present invention, each of the first arm 3 and second arm 5 of the planar Hall resistive sensor is preferably a spin-valve-type sensor thin film structure formed by depositing the following layers on the underlying substrate 1:

a underlayer 10 deposited on the underlying substrate 1;

a first ferromagnetic layer 20 deposited on the underlayer 10;

a spacer layer 30 deposited on the first ferromagnetic layer 20;

a second ferromagnetic layer 40 deposited on the spacer layer 30;

an anti-ferromagnetic layer 50 deposited on the second ferromagnetic layer 40; and a capping layer 60 deposited on the anti-ferromagnetic layer 50.

More preferably, the underlayer 10 forming the first arm and second arm of the planar Hall resistive sensor may be formed of Ta or Ti; the first ferromagnetic layer 20 may be formed of nickel iron (NiFe), nickel cobalt (NiCo) or cobalt iron (CoFe); the spacer layer 30 may be formed of any one selected from the group consisting of Cu, Ta, rubidium (Ru) and Pd; the second ferromagnetic layer 40 may be formed of nickel iron (NiFe), nickel cobalt (NiCo) or cobalt iron (CoFe); the anti-ferromagnetic layer 50 may be formed of any one selected from the group consisting of IrMn, NiO, FeMn and PtMn; and the capping layer 60 may be formed of tantalum (Ta) or titanium (Ti).

With respect to the thicknesses of the layers forming the arms according to the present invention, the underlayer 10 may be formed of tantalum (Ta) or titanium (Ti) to a thickness of 1-20 nm.

The first ferromagnetic layer 20 may be formed of cobalt-iron (CoFe), nickel cobalt (NiCo) or nickel-iron (NiFe) to a thickness of 1-20 nm.

The spacer layer 30 may be formed of any one non-magnetic material selected from among copper (Cu), tantalum (Ta), rubidium (Ru) and palladium (Pd) to a thickness of 1-10 nm.

The second ferromagnetic layer 40 may be formed of cobalt-iron (CoFe), nickel cobalt (NiCo) or nickel-iron (NiFe) to a thickness of 1-20 nm.

The anti-ferromagnetic layer 50 may be formed of any one selected from among IrMn, nickel oxide (NiO), FeMn and PtMn to a thickness of 10-100 nm.

The capping layer 60 may be formed of tantalum (Ta) or titanium (Ti) to a thickness of 5-20 nm in the same manner as the underlayer.

Meanwhile, the underlying substrate 1 may be made of silicon dioxide (SiO2), silicon (Si), glass, quartz or the like, but the material of the underlying substrate 1 is not specifically limited, as long as it can be used for sensor substrates.

Further, according to the present invention, either the current electrodes 2 at both ends of the first arm 3 or the voltage electrodes 4 at both ends of the second arm 5 may be composed of a tantalum (Ta) layer and a layer deposited on the tantalum layer and made of any one selected from the group consisting of Au, Cu and Ag.

Preferably, each of the current electrodes and the voltage electrodes may be composed of a 1-10 nm thick tantalum (Ta) layer and a 5-500 nm thick layer deposited on the tantalum layer and made of any one selected from the group consisting of gold (Au), copper (Cu) and silver (Ag).

Specifically, the active junction area 6 is the key portion of the planar Hall resistive sensor. In the active junction area 6, a magnetic signal from a substantially magnetized superparamagnetic nanoparticle bead is converted into an electrical signal (voltage difference), and the first arm and the second arm, which are formed by sputtering and form two axes, cross each other. The active junction area 6 may have various shapes, including square, circular and rectangular shapes.

The susceptibility of the active junction area can be increased by controlling the length of the first arm. Specifically, superparamagnetic nanoparticle beads show magnetic properties when an external magnetic field is applied, but lose the magnetic properties upon removal of the external electric field. Thus, the superparamagnetic nanoparticle beads are influenced not only by an external magnetic field ($H_{app}$), but also by an induced magnetic field generated by a magnetic material. For example, when a magnetic material such as a magnetic sensor is present near a superparamagnetic nanoparticle bead, the superparamagnetic nanoparticle bead is magnetized by the applied external magnetic field ($H_{app}$) to form a stray magnetic field, and an induced magnetic field is formed in the magnetic sensor by the stray magnetic field ($H_{stray}$), and as a result, the intensity of the applied external magnetic field becomes different from the intensity of the effective magnetic field ($H_{eff}$) in the sensor. However, when no magnetic material is present near the superparamagnetic nanoparticle bead, an induced magnetic field is not present, and thus the intensity of the external magnetic field can be equal to the intensity of the effective magnetic field in the sensor. Thus, when the intensity of the effective magnetic field in the sensor is controlled to be equal to the intensity of the external magnetic field as shown in the following equation 1, the magnetic susceptibility of a single superparamagnetic nanoparticle bead can be measured using the following equations 1 and 2:

$$H_{eff} = H_{app} - H_{stray} \qquad \text{Equation 1}$$

Wherein $H_{eff}$ is the effective magnetic field in the sensor, $H_{app}$ is the applied external magnetic field, and $H_{stray}$ tray is a stray magnetic field generated from the magnetized magnetic bead.

$$\chi_V = \frac{1}{S} \frac{\Delta V}{H_{eff}} \bigg|_{H_{app}} \frac{4\pi r^3}{V_{bead}} \qquad \text{Equation 2}$$

wherein S is the sensitivity of the sensor, $\Delta V$ is the change in the sensor output voltage, caused by the stray magnetic field, $\chi V$ is the magnetic susceptibility of the superparamagnetic nanoparticle bead, $V_{bead}$ is the volume of the superparamagnetic nanoparticle bead, $H_{eff}$ is the effective magnetic field in the sensor, and r is the distance between the sensor and the nanoparticle bead.

When the intensity of the external magnetic field is maintained at a constant level, the distortion of magnetic field contours that appear in the planar Hall resistive sensor differs depending on the length of the first arm 3, and the magnetic field contours are concentrated at the edge of the active junction area 6. Thus, when the length of the arm in the planar Hall resistive sensor is controlled, an induced magnetic field which is generated from the sensor can be controlled.

Thus, according to the present invention, when the length of the first arm 3 in the planar Hall resistive sensor is controlled regardless of the shape of the active junction area 6 of the planar Hall resistive sensor so that the intensity of the average effective magnetic field in the sensor is equal to the intensity of an external magnetic field, the magnetic susceptibility of a superparamagnetic nanoparticle bead can be measured.

In the microfluidic chip according to the present invention, the microfluidic channels 11, 12 and 13 may have a T-shaped microfluidic channel structure comprising: a continuous phase fluid and a microfluidic channel 11 through which the continuous phase fluid moves; a magnetic fluid and a microfluidic channel through which the magnetic fluid moves; and a superparamagnetic nanoparticle bead droplet formed at a position at which the two channels 11 and 12 meet each other, and a microfluidic channel 13 through which the formed droplet moves.

The microfluidic channels 11, 12 and 13 may be made of polydimethylsiloxane (PDMS).

Because the fluids that pass through the microfluidic channels are organic solutions, the hydrophobic surface of the PDMS can be hydrophilically modified so that the solutions can easily flow in the channels.

For example, the microfluidic channels can be treated by introducing a 10% tetraethoxysilane (TEOS)-containing ethanol solution into the channels, coating the channels with the solution for a predetermined time, and washing the channels with ethanol, followed by drying in a vacuum.

In the microfluidic chip according to the present invention, the microfluidic channels 11, 12 and 13 may further comprise: a first inlet port 14 for injecting the continuous phase fluid into the microfluidic channel 11 through which the continuous phase fluid moves; a second inlet port 15 for injecting the magnetic fluid into the microfluidic channel 13 through which the magnetic fluid moves; and an outlet port 16 for discharging the continuous phase fluid and the magnetic fluid droplet from the chip after passage over the active junction area 6.

The continuous phase fluid 11 that is injected into the microfluidic channel 11 is preferably a mixed solution of polyethylene glycol and sodium dodecylsulfate.

The magnetic fluid that is used in the present invention is preferably a dispersion of superparamagnetic nanoparticle beads in the organic solvent hexadecane.

Generally, the magnetic nanoparticles of the magnetic fluid are synthesized in an organic solvent. Thus, the magnetic nanoparticles can be effectively dispersed using an organic solvent in place of an aqueous solvent as a dispersing medium. The effectively dispersed nanoparticles in droplets enable the magnetic susceptibility to be more accurately measured.

From this point of view, the organic solvent that is used in the present invention is more preferably hexadecane.

In addition, in the microfluidic chip according to the present invention, the continuous phase fluid and magnetic fluid of the microfluidic channels enable the size of a magnetic fluid droplet at the T-shaped intersection to be controlled by controlling air pressure.

Figure 5:
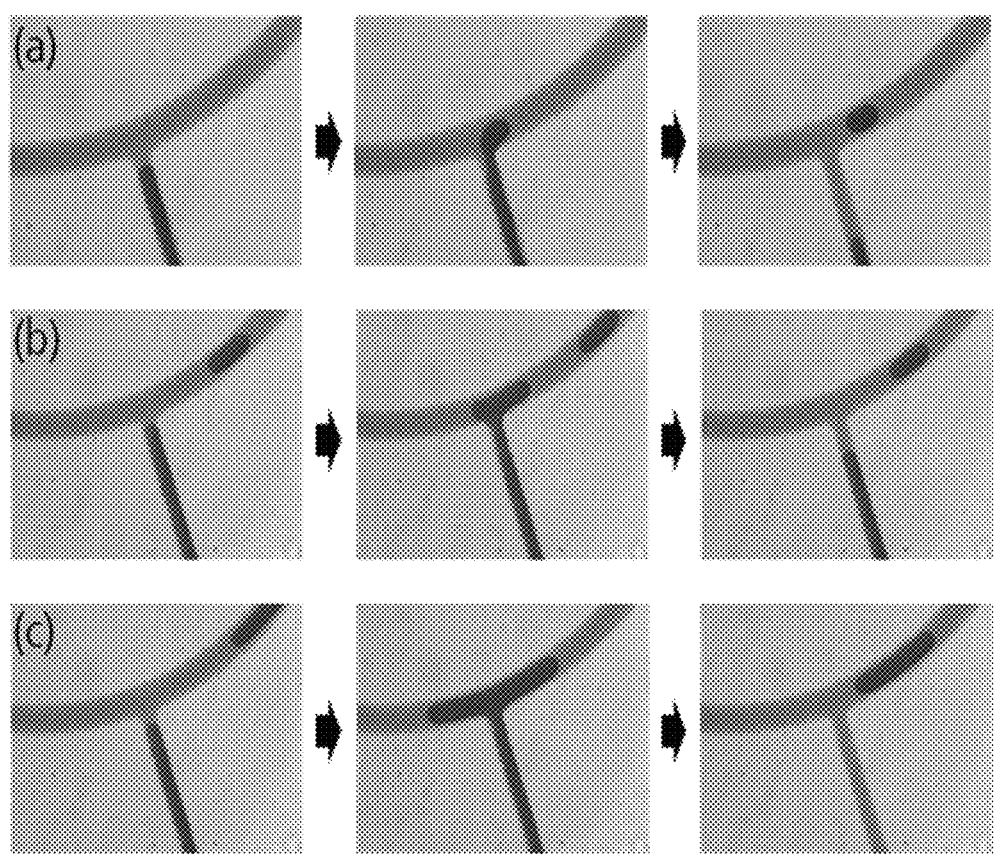
FIG. 5 shows processes in which superparamagnetic nanoparticle bead droplets having different lengths are formed by controlling pressure using an air pressure control unit (not shown) connected with a first inlet port 14 and a second inlet port 15 according to an embodiment of the present invention, and specifically.
Figure 6:
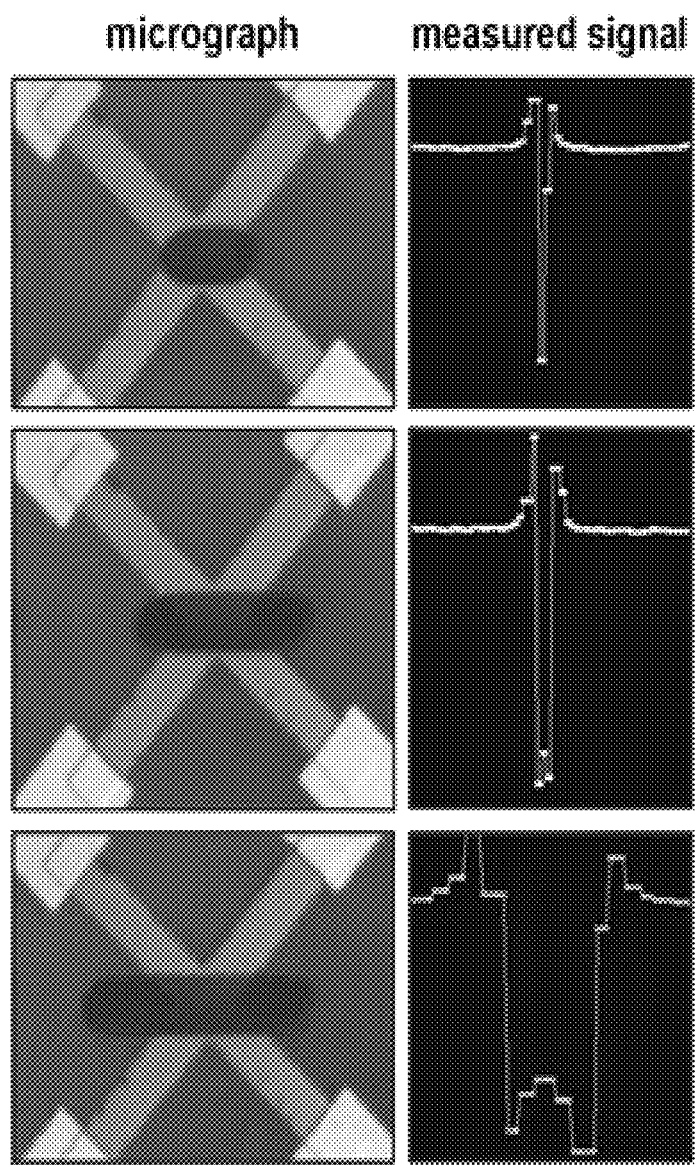
FIG. 6 is a set of photographs showing the results of microscopically observing magnetic fluid droplets having different sizes while measuring a signal sensed by a voltage electrode 4 when pressure controlled by an air pressure control unit connected with a first inlet port 14 and a second inlet port 15 is applied according to an embodiment of the present invention (left: a micrograph of a magnetic fluid flowing through a magnetic sensor; and right: a signal photograph of a magnetic field emitted from a magnetic fluid, measured by a sensor)

When air pressure which is applied to the magnetic fluid is changed, the length of the magnetic fluid droplet flowing in the channel can be changed (FIG. 5). Depending on the length of the magnetic fluid droplet, the shape of the signal changes. FIG. 6 shows the shape of the signal according to the length of the magnetic fluid droplet. The sizes of the maximum and minimum signals are similar regardless of the length of the droplet. It appears that the shape of the measured signal is similar to the simulated signal shape, because the residence time of the magnetic fluid droplet on the sensor increases as the length of the magnetic fluid droplet increases. Further, this may also be because of the difference in size between the droplet and the magnetic sensor. Thus, when a smaller magnetic sensor is used, results as shown in FIG. 5(*c*) can be obtained even in a smaller droplet. In addition, when the time resolution is improved, the accuracy of measurement results can be improved even under conditions as shown in FIG. 5.

The present invention also provides a method for measuring the magnetic susceptibility of a superparamagnetic nanoparticle bead using the above-described microfluidic chip.

Hereinafter, the above measurement method will be described in detail.

The inventive method for measuring the magnetic susceptibility of a superparamagnetic nanoparticle bead comprises the steps of: (1) injecting a continuous phase fluid and a magnetic fluid into a continuous phase fluid-moving microfluidic channel and a magnetic fluid-moving microfluidic channel, respectively, in a microfluidic chip;

(2) allowing the continuous phase fluid and the magnetic fluid, injected in step (1), to meet each other to form a superparamagnetic nanoparticle bead droplet; and (3) measuring the magnetic susceptibility of a superparamagnetic nanoparticle bead in the droplet when the superparamagnetic nanoparticle bead droplet formed in step (2) passes over the active junction area of a planar Hall resistive sensor.

Hereinafter, each step of the measurement method of the present invention will be described in detail.

Step (1) of the measurement method of the present invention is a step of injecting the continuous phase fluid and the magnetic fluid into the microfluidic channels 11 and 12 of the microfluidic chip in order to form a droplet having dispersed therein superparamagnetic nanoparticle beads whose magnetic susceptibility is to be measured.

Preferably, the continuous phase fluid that is used in step (1) may be a mixed solution of polyethylene glycol and sodium dodecylsulfate.

In addition, the magnetic fluid that is used in step 1 may be a dispersion of superparamagnetic nanoparticle beads in the organic solvent hexadecane.

The size of the superparamagnetic nanoparticle bead droplet that is formed at the intersection of the T-shaped microfluidic channel can be controlled by controlling the injection pressure of the continuous phase fluid and the magnetic fluid.

When air pressure which is applied to the magnetic fluid is changed, the length of the magnetic fluid droplet flowing in the channel can be changed (FIG. 5). Depending on the length of the magnetic fluid droplet, the shape of the signal changes. FIG. 6 shows the shape of the signal according to the length of the magnetic fluid droplet. The sizes of the maximum and minimum signals are similar regardless of the length of the droplet. It appears that the shape of the measured signal is similar to the simulated signal shape, because the residence time of the magnetic fluid droplet on the sensor increases as the length of the magnetic fluid droplet increases. Further, this may also be because of the difference in size between the droplet and the magnetic sensor. Thus, when a smaller magnetic sensor is used, results as shown in FIG. 5(*c*) can be obtained even in a smaller droplet. In addition, when the time resolution is improved, the accuracy of measurement results can be improved even under conditions as shown in FIG. 5.

Step (2) of the measurement method of the present invention is a step of forming a droplet having dispersed therein superparamagnetic nanoparticle beads whose magnetic susceptibility is to be measured.

The droplet can be produced in a size enabling the magnetic susceptibility to be measured as accurate as possible at the T-shaped microfluidic channel interaction at which the magnetic fluid and the continuous phase fluid meet each other as described above.

Step 3 of the measurement method of the present invention is a step of measuring superparamagnetic nanoparticle beads in the droplet produced in step (2).

The magnetic susceptibility of the superparamagnetic nanoparticle bead can be measured by controlling the length of the first arm 3 of the planar Hall resistive sensor so as to satisfy the condition shown in the following equation 1 when the superparamagnetic nanoparticle bead drop passes over the active junction area of the planar Hall resistive sensor through the intersection of the T-shaped microfluidic channel structure:

$$H_{eff} = H_{app} - H_{stray}$$ Equation 1 wherein $H_{eff}$ is the effective magnetic field in the sensor, $H_{app}$ is an applied external magnetic field, and $H_{stray}$ is a stray magnetic field generated from the magnetized magnetic beads.

The above-described microfluidic chip and the measurement method employing the same can accurately measure the magnetic susceptibility of superparamagnetic nanoparticle beads.

The present invention also provides a planar Hall resistive sensor for measuring the magnetic susceptibility of a superparamagnetic nanoparticle bead, the sensor comprising an active junction area for sensing the superparamagnetic nanoparticle bead, which protrudes from an underlying substrate and in which a first arm 3 having current electrodes 2 at both ends and a second arm 5 having voltage electrodes 4 at both ends cross each other, wherein the length of the first arm 3 is controlled.

Specifically, according to the present invention, the influence of a stray magnetic field, which is generated from the bead magnetized by an external magnetic field, on the sensor, is minimized, and thus the magnetic susceptibility of the superparamagnetic nanoparticle bead can be measured by controlling the length of the arm protruding from the active junction area so that the intensity of the effective magnetic field shown in the following formula 1 most closely approaches the intensity of an applied external magnetic field:

$$H_{eff} = H_{app} - H_{stray}$$ Equation 1 wherein $H_{eff}$ is the effective magnetic field in the sensor, $H_{app}$ is an applied external magnetic field, and $H_{stray}$ is a stray magnetic field generated from the magnetized magnetic bead.

The magnetic susceptibility of the superparamagnetic nanoparticle bead can be calculated using the following equation 3:

$$\Delta V = S \cdot \Delta H_{stray} \text{ with } \Delta H_{stray} = -\frac{\chi_V V_{bead}}{4\pi z^3} H_{eff}$$ Equation 3 wherein $\Delta H_{stray}$ is the stray magnetic field of the superparamagnetic nanoparticle bead magnetized by the external magnetic field, S is the sensitivity of the sensor, $\Delta V$ is the change in the sensor output voltage, caused by the stray magnetic field, $\chi_v$ is the magnetic susceptibility of the superparamagnetic nanoparticle bead, $V_{bead}$ is the volume of the superparamagnetic nanoparticle bead, z is the distance between the sensor and the superparamagnetic nanoparticle bead, and $H_{eff}$ is the effective magnetic field in the sensor.

A superparamagnetic nanoparticle bead is a material which shows magnetic properties when an external magnetic field is applied, but loses the magnetic properties upon removal of the applied external electric field. Thus, the superparamagnetic nanoparticle bead is influenced not only by an external magnetic field, but also by an induced magnetic field generated by a magnetic material. For example, when a magnetic material such as a magnetic sensor is present near a superparamagnetic nanoparticle bead, the superparamagnetic nanoparticle bead is magnetized by the applied external magnetic field to form a stray magnetic field, and an induced magnetic field is formed in the magnetic sensor by the stray magnetic field, and as a result, the intensity of the applied external magnetic field becomes different from the intensity of the effective magnetic field in the sensor. However, when no magnetic material is present near the superparamagnetic nanoparticle bead, an induced magnetic field is not present, and thus the intensity of the external magnetic field can be equal to the intensity of the effective magnetic field in the sensor. Thus, when the intensity of the effective magnetic field in the sensor is controlled to be equal to the intensity of the external magnetic field as shown in the following equation 2, the magnetic susceptibility of a single superparamagnetic nanoparticle bead can be measured:

$$\chi_V = \frac{1}{2.61 \times 10^{-6} \text{ V/Oe}} \times \frac{14.83 \times 10^{-6} \text{ V}}{9.2954 \text{ Oe}} \times \frac{4\pi (8.7 \times 10^{-6} \text{ m})^3}{40 \times 10^{-5} \text{ m}^3}$$

$$\chi_V = 0.126.$$

Considering the above-described characteristics of the superparamagnetic nanoparticle bead, it can be seen that the intensity of the effective magnetic field in the sensor can approach the intensity of an applied external magnetic field as the distance between the superparamagnetic nanoparticle bead and the sensor increases.

Figure 11:
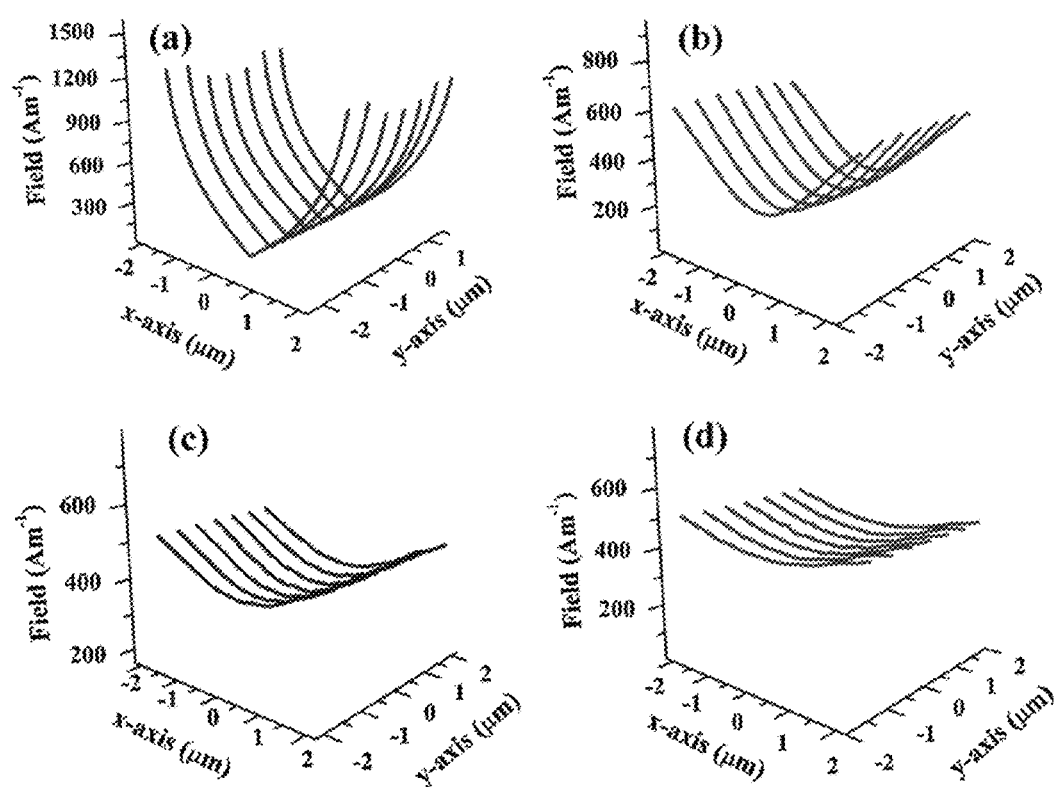
FIG. 11 shows the spatial distribution of a magnetic field in a square active junction area having a side length of 3 μm as a function of the distance (z) between the active junction area and a superparamagnetic bead when an external magnetic field having an intensity of 477.48 A·m$^{-1}$ is applied to the active junction area in the x-axis direction (FIG. 11(a): z=0, FIG. 11(b): z=1 μm, FIG. 11(c): z=2 μm, and FIG. 11(d): z=2.5 μm)

FIG. 11 shows the spatial distribution of a magnetic field in an active junction area having a side length of 3 μm as a function of the distance (z) between the active junction area and a superparamagnetic nanoparticle bead when an external magnetic field having an intensity of 477.48 A·m$^{-1}$ is applied to the active junction area in the x-axis direction.

Referring to FIG. 11(a), it can be seen that the magnetic field intensity of the active junction area in the same line as the direction in which the external magnetic field (x axis=0) is smaller than the intensity of the applied external magnetic field. On the other hand, it can be seen that the magnetic field intensity of the active junction area becomes significantly higher than the intensity of the external magnetic field as it is closer to the edge of the active junction area. In addition, referring to FIGS. 11(a) to 11(d), as the distance between the superparamagnetic bead and the active junction area increases, the spatial distribution of a magnetic field in the active junction area shows a more fluent curve, and the magnetic field intensity of the active junction area more approaches the intensity of the applied external magnetic field. Thus, it can be seen that, as the distance between the superparamagnetic bead and the sensor increases, the intensity of the effective magnetic field in the sensor more approaches the intensity of the applied external magnetic field.

As described above, when the distance between the superparamagnetic bead and the sensor is increased, the intensity of the effective magnetic field in the sensor can be controlled to be equal to the intensity of the external magnetic field. However, in this case, the difference in voltage in the sensor, which is required to determine the magnetic susceptibility of the superparamagnetic bead, actually becomes unclear, and thus the increase in the distance cannot be an alternative for measuring the magnetic susceptibility of the superparamagnetic bead in the sensor.

Figure 12:
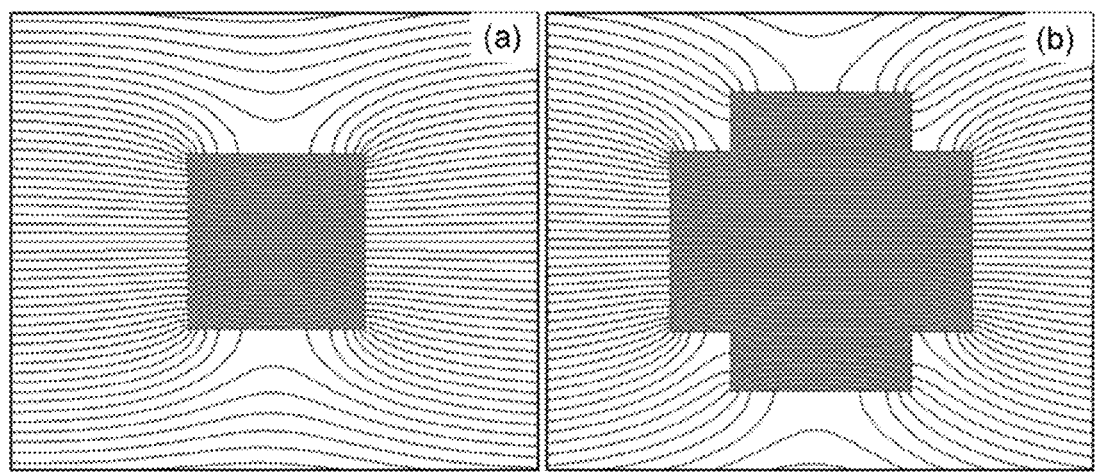
FIG. 12 shows magnetic field contours near nickel-iron (NiFe) having arm lengths of 3 μm (a) and 7 μm (b), respectively, when an external magnetic field is applied with an intensity of 477.48 A·m$^{-1}$ in the x-axis direction.

FIG. 12 shows magnetic field contours near nickel-iron (NiFe) sensors in which the lengths of the arms of the active junction area are 3 µm (a) and 7 µm (b), respectively, when an external magnetic field having an intensity of 477.48 A·m$^{-1}$ was applied in the x-axis direction. Referring to FIG. 12, it can be seen that, when the intensity of the external magnetic field is maintained at a constant level, the distortion of magnetic field contours appearing in the sensor changes depending on the length of the arm. In addition, it can be seen that the magnetic field contours are concentrated at the edge of the active junction area. These results suggest that the length of the arm in the planar Hall resistive sensor is a parameter for controlling the active junction area fixed in the sensor. Thus, an induced magnetic field which is formed in the sensor can be controlled by controlling the length of the arm of the planar Hall resistive sensor.

Thus, according to the present invention, when the length of the arm protruding from the active junction area of the planar Hall resistive sensor is controlled regardless of the shape of the active junction area of the planar Hall resistive sensor so that the intensity of the average effective magnetic field in the sensor approaches the intensity of an external magnetic field, the magnetic susceptibility of a superparamagnetic nanoparticle bead can be measured.

In the present invention, the planar Hall resistive sensor comprises electrodes at the end portions of the protruding cross-shaped arms. Specifically, the end portions of the protruding cross-shaped arms comprise current electrodes for measuring an applied electric current and voltage electrodes for measuring a voltage resulting from the current electrodes and the Hall effect caused by application of an external magnetic field. In addition, the current electrodes and the voltage electrodes are located in the same line. Specifically, a straight line connecting the current electrodes to each other is perpendicular to a straight line connecting the voltage electrodes to each other.

Moreover, the active junction area included in the planar Hall resistive sensor may have a square, circular or rectangular shape. In addition, it may be of any shape that can have cross-shaped protruding arms.

Figure 13:
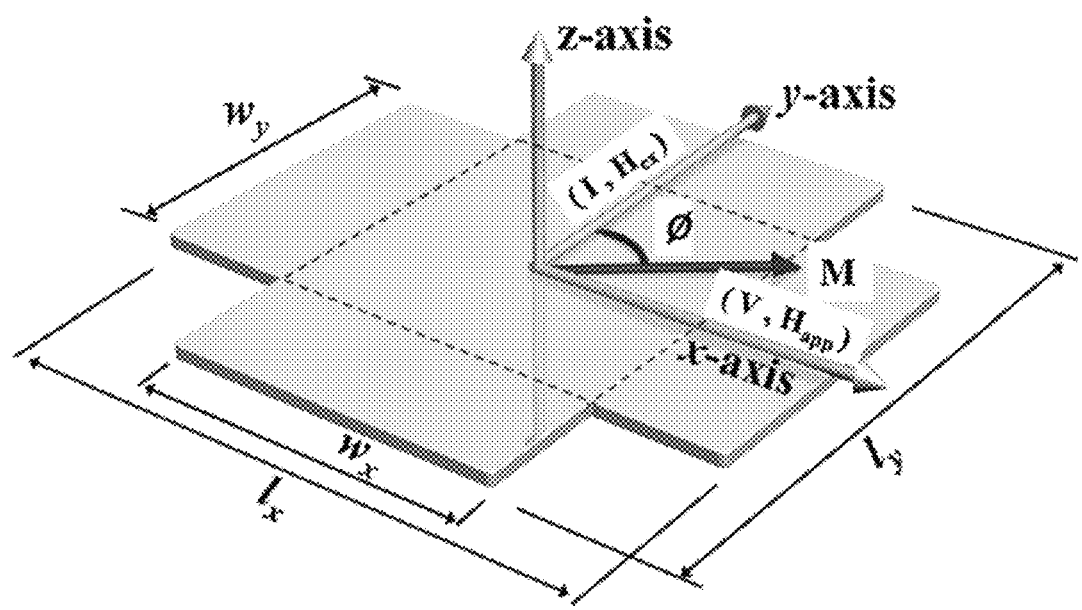
FIG. 13 schematically shows a cross-shaped planar Hall resistive sensor according an embodiment of the present invention.
Figure 14:
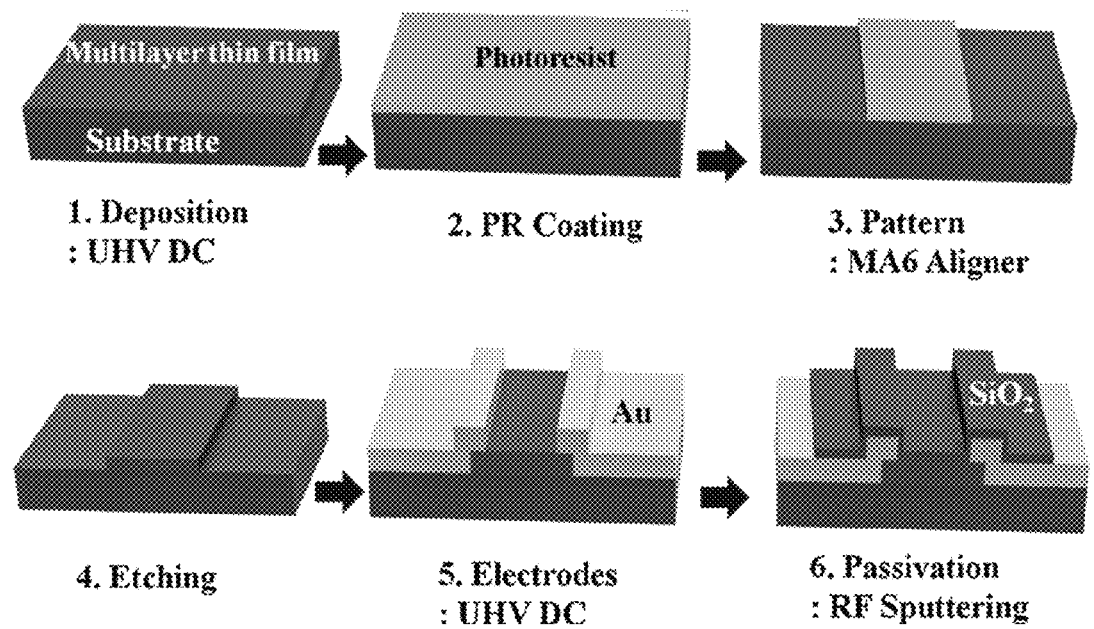
FIG. 14 schematically shows a method for fabricating a cross-shaped planar Hall resistive sensor according to an embodiment of the present invention.
Figure 15:
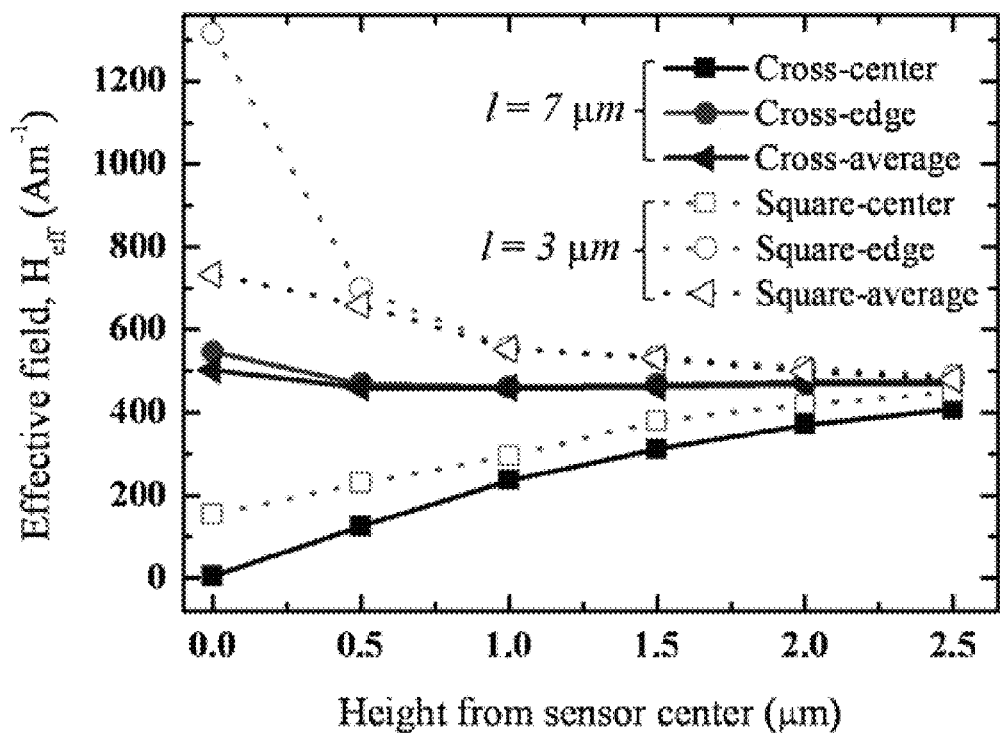
FIG. 15 shows the results of measuring the effective magnetic fields in the center and edge of cross-shaped planar Hall resistive sensors of Example 1 of the present invention and Comparative Example 3, and the average effective magnetic field, at different heights from the surface of the sensors.
Figure 16:
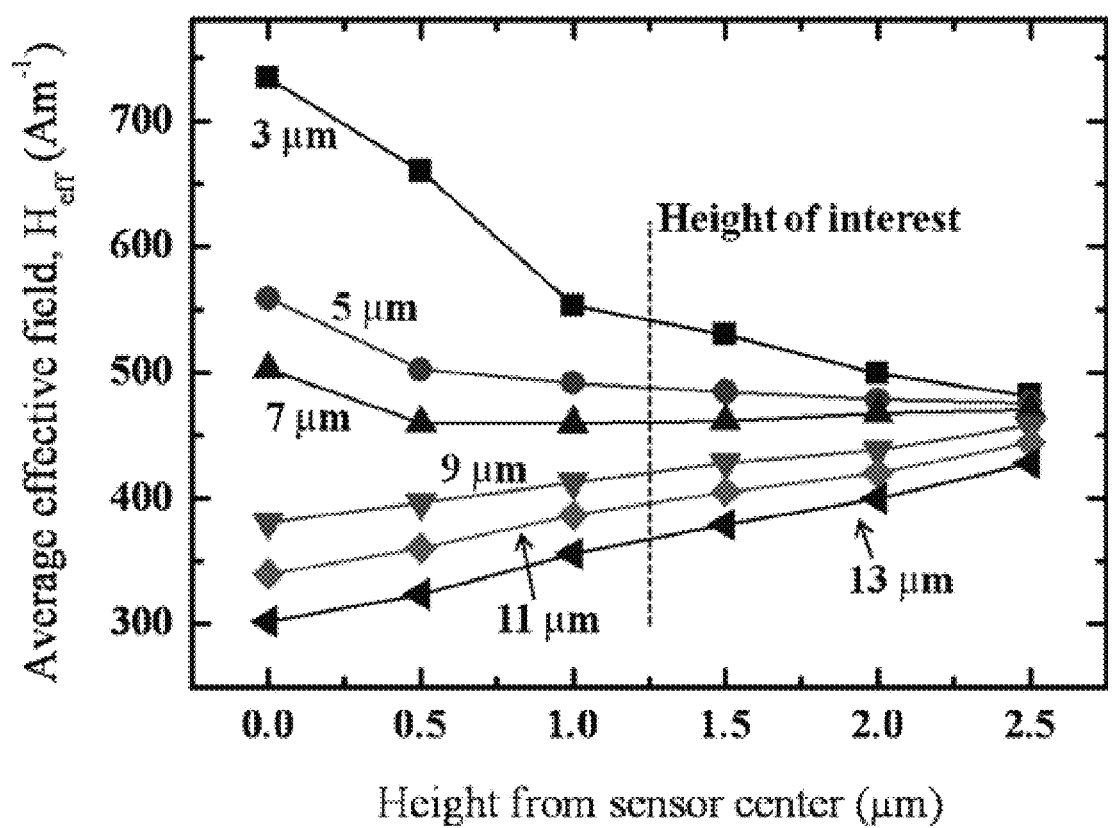

For example, FIG. 13 schematically shows a cross-shaped planar Hall resistive sensor comprising a square active junction area. As shown in FIG. 13, the cross-shaped planar Hall resistive sensor has a shape in which arms protrude from the active junction area. In FIG. 13, $l_x$ and $l_y$ represent the lengths of the arms of the cross-shaped planar Hall resistive sensor, and $W_x$ and $W_y$ represent the lengths of the sides of the active junction area.

In the present invention, the planar Hall resistive sensor may comprise a square active junction area having a side length ranging from 100 nm to 10 µm, but the side length is not limited to this range, because the size of the active junction area can be selected depending on the size of the superparamagnetic bead to be analyzed. For example, when the magnetic susceptibility of a superparamagnetic bead (Dynabed®-280) having a diameter of 2.8 µm is to be measured, a cross-shaped planar Hall resistive sensor having a side length of 3 µm may be used.

In addition, the intensity of an external magnetic field which is applied in order to measure the magnetic susceptibility of a superparamagnetic bead is not specifically limited, because the length of the arms of the cross-shaped planar Hall resistive sensor is controlled so that the intensity of the effective magnetic field in the sensor can approach the intensity of the applied external magnetic field.

For example, when the magnetic susceptibility of a superparamagnetic bead having a size of 2.9 µm was measured by applying an external magnetic intensity having an intensity of 477.28 A·m$^{-1}$, the intensity of the effective magnetic field in a cross-shaped planar Hall resistive sensor (Example 1) having an arm length of about 7 µm and a side long of 3 µm was similar to the intensity of the applied external magnetic field.

The present invention also provides a method for measuring the magnetic susceptibility of a superparamagnetic nanoparticle bead using the planar Hall resistive sensor of the present invention, wherein the length of the first arm in the planar Hall resistive sensor is controlled to minimize the influence of a stray magnetic field so as to the satisfy the condition shown in the following equation 1:

$$H_{eff} = H_{app} - H_{stray} \qquad \text{Equation 1}$$

wherein $H_{eff}$ is the effective magnetic field in the sensor, $H_{app}$ is the applied external magnetic field, and $H_{stray}$ is a stray magnetic field which is generated from a magnetized magnetic bead.

Specifically, in a step of measuring the effective magnetic field in the planar Hall resistive sensor according to the present invention, a magnetic bead droplet having a specific size is dropped onto the active junction area of the planar Hall resistive sensor, after which an external magnetic field is applied to the planar Hall resistive sensor, and the effective magnetic fields in the center and edge of the sensor are measured and averaged.

Then, planar Hall resistive sensors having different arm lengths are fabricated, and the effective magnetic field in each of the fabricated planar Hall resistive sensors is calculated by repeating the above.

This is followed by a step of measuring the magnetic susceptibility of the superparamagnetic bead using the planar Hall resistive sensor having the arm length corresponding to the case in which the effective magnetic field most closely approaches the applied external magnetic field. In this manner, the magnetic susceptibility of the superparamagnetic nanoparticle bead can be accurately measured.

Hereinafter, the present invention will be described in further detail with reference to examples. It is to be understood, however, that these examples are for illustrative purposes only and are not intended to limit the scope of the present invention.

Example 1

Fabrication of Planar Hall Resistive Sensor

A planar Hall resistive sensor was fabricated on a glass substrate having a size of 30 mm×30 mm by repeating photolithographic and sputtering processes.

1. Photolithography

Photoresist (Az 5214, AZ Electronic Materials) was dropped onto a glass substrate, after which it was spin-coated using a spin coater at 3000 RPM for 30 seconds and heat-treated at 120° C. for 1 minute. A mask was aligned on the heat-treated substrate using a mask aligner (MDA 400S, MIDAS SYSTEM. Korea), followed by exposure to light for 10 seconds. The exposed substrate was developed with an AZ developer for 1 minute, and then washed in distilled water.

2. Deposition of Planar Hall Resistive Sensor by Sputter

Figure 3:
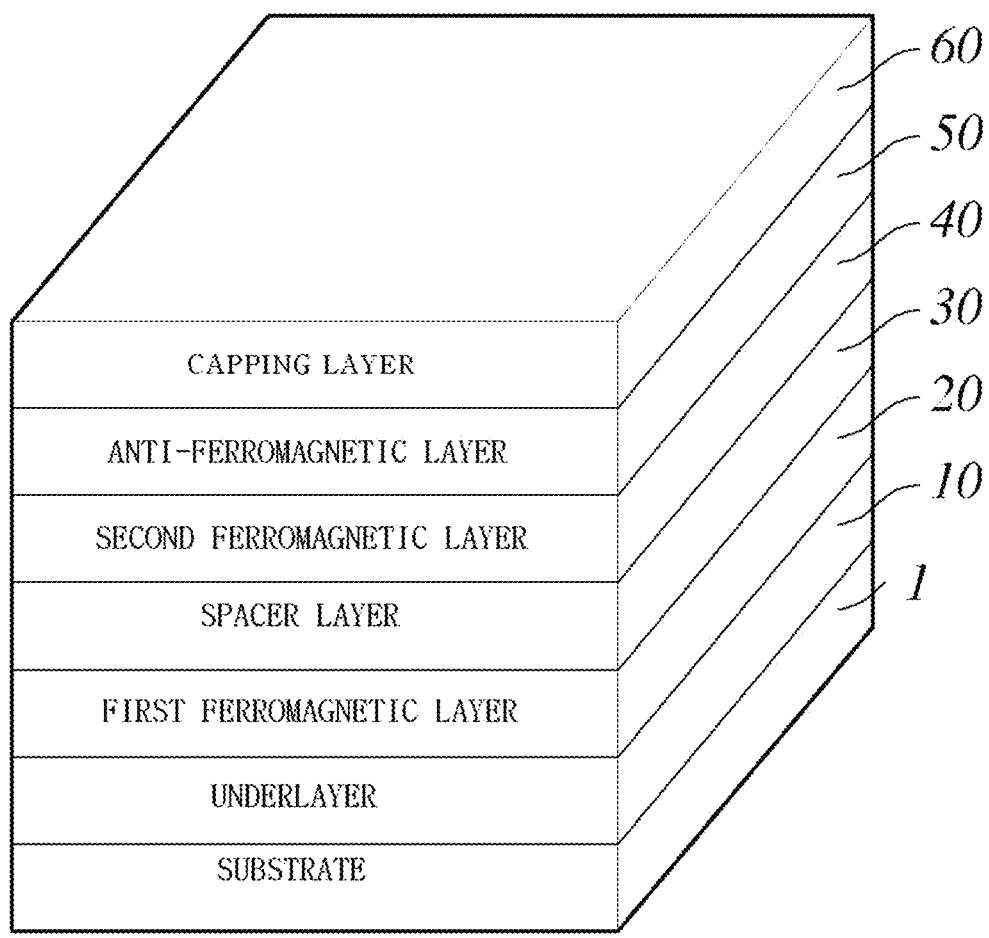
FIG. 3 shows the stack structure of a first arm 3 or a second arm 5 according to an embodiment of the present invention.
Figure 4:
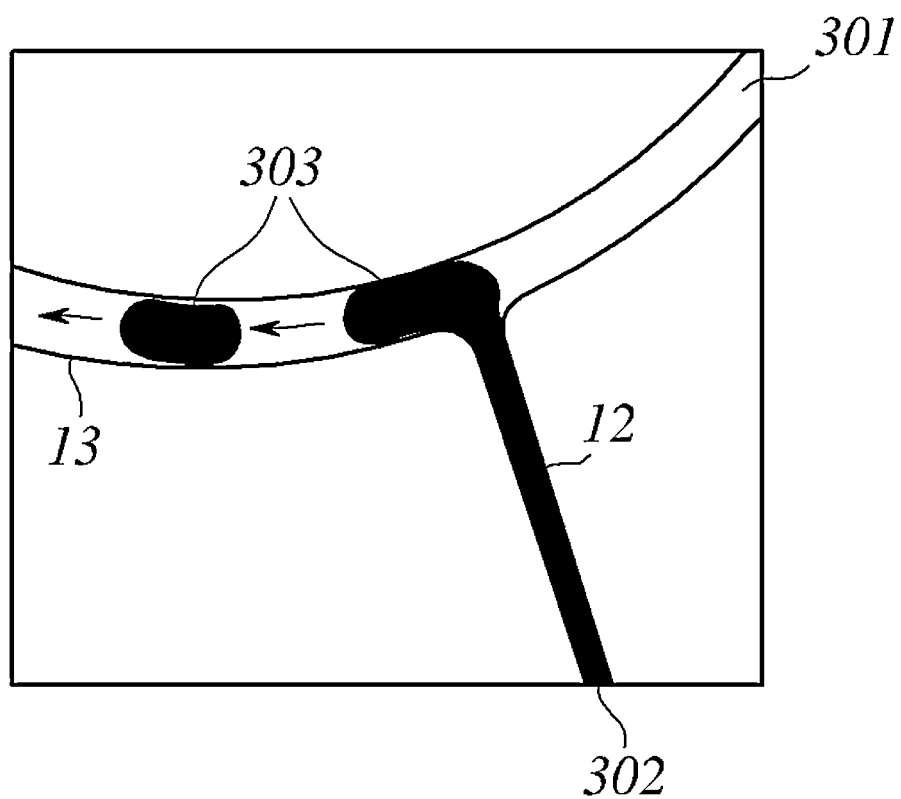
FIG. 4 shows the structure of a T-shaped microfluidic channel according to an embodiment of the present invention, in which a superparamagnetic nanoparticle bead droplet is formed and flows in the arrow direction.

After the photolithographic process, the substrate was placed in a magnetron sputter, and a sensor layer was deposited on the substrate. The sensor had a spin valve structure consisting of Ta (6 nm), nickel-iron (NiFe) (10 nm), Cu (1.2 nm), nickel-iron (NiFe) (2 nm), IrMn (10 nm) and Ta (6 nm), which were sequentially deposited in that order (FIG. 3). Herein, the magnitude of the electric current used was maintained at 100 mA using a DC power source, and the deposition was performed at a pressure of $3 \times 10^{-3}$ Torr in an Ar atmosphere. During the deposition, a magnetic field was applied to the substrate in one direction using a magnet so that the sensor was divided into an axis in which current electrodes were to be connected to both ends of an arm and another axis in which current electrodes were to be connected to both ends of an arm. After completion of the deposition, the photoresist was removed from the substrate using acetone. Using the same process, voltage and current electrodes connected to the sensor were formed using Cu and Au. The fabricated planar Hall resistive sensor was of a cross type and had a size of 50 μm×50 μm. In addition, the fabricated cross-shaped planar Hall resistive sensor had an arm length of 7 μm and included a square active junction area having a side length of 3 μm.

Example 2

Fabrication of Microfluidic Chip

1. Formation of Microfluidic Channels 1-1. Fabrication of Mold by Photolithography First, a mold was fabricated on a 3 inch silicon substrate by a photolithographic process. The silicon substrate used had a 500 nm thick $SiO_2$ layer at one side and was ultrasonically washed with acetone for 30 min and methanol for 30 min. SU-8 2015 (MICROCHEM) photoresist was spin-coated on the washed silicon substrate to a thickness of 10 μm using a spin coater (SPIN 1200D, MIDAS SYSTEM. Korea) at 2000 RPM. The photoresist-coated substrate was heat-treated in an oven at 70° C. for 2 minutes, and then heat-treated in an oven at 100° C. for 5 minutes. A mask was aligned on the heat-treated substrate in a mask aligner, and then exposed to light for 5 minutes. After exposure to light, the substrate was heat-treated in an oven at 70° C. for 1 minute, and then heat-treated in an oven at 100° C. for 2 minutes. The heat-treated substrate was developed in an SU developer, and then washed sequentially with acetone, isopropanol and ethanol and dried with nitrogen gas, thereby fabricating a mold required for the fabrication of microfluidic channels.

1-2. Preparation and Curing of PDMS Mixture

As a material for making microfluidic channels, polydimethylsiloxane (PDMS; SYLGARD® 184 (Dow Corning, USA)) was used. PDMS as a main component and a curing agent were mixed with each other at a ratio of 10:1 and completely debubbled in a vacuum chamber. Then, the mixture was poured on the above-fabricated mold and cured by heating at 70° C. for 2 hours.

2. Fabrication of Microfluidic Chip Comprising Planar Hall Resistive Sensor

The inlet and outlet portions of the planar Hall resistive sensor and the channel structure were perforated with a punch, and each microfluidic channel was treated with $O_2$ plasma using a plasma generator (CUTE, FEMTO SCI-ENCE, Korea) at 100 W for 90 seconds. The plasma-treated magnetic sensor and channel were accurately aligned with each other and attached to each other, followed by heating in an oven at 70° C. for 15 minutes, thereby fabricating a microfluidic chip. In order to change the hydrophobic surface of the PDMS, an ethanol solution containing 10% tetraethoxysilane (TEOS) (Sigma, USA) was injected into the microfluidic channels, and the microfluidic channels were coated with the ethanol solution for 1 hour. Then, the microfluidic channels were washed with ethanol and dried in a vacuum.

Example 3

Measurement of Magnetic Susceptibility of Superparamagnetic Nanoparticle Bead Using Microfluidic Chip 1. Measurement of Magnetic Fluid Flowing in Microfluidic Chip In order to measure a magnetic fluid flowing in the microfluidic chip under visual observation, a microscope was placed on a Helmholtz coil and connected to a monitor. In order to accurately measure a signal when a magnetic fluid flowing in the channel passes over the sensor, a microscopic program capable of observing the movement of the magnetic fluid and a Labview program capable of measuring the change in the signal in the sensor were provided in a single computer, and a system was designed such that two sets of data could be simultaneously observed on a single monitor. The microfluidic chip including the planar Hall resistive sensor was located at the center of a Helmholtz coil. The profile of the planar Hall resistive sensor was measured, and a magnetic field corresponding to the highest sensitivity of the sensor was applied to the Helmholtz coil.

Figure 8:
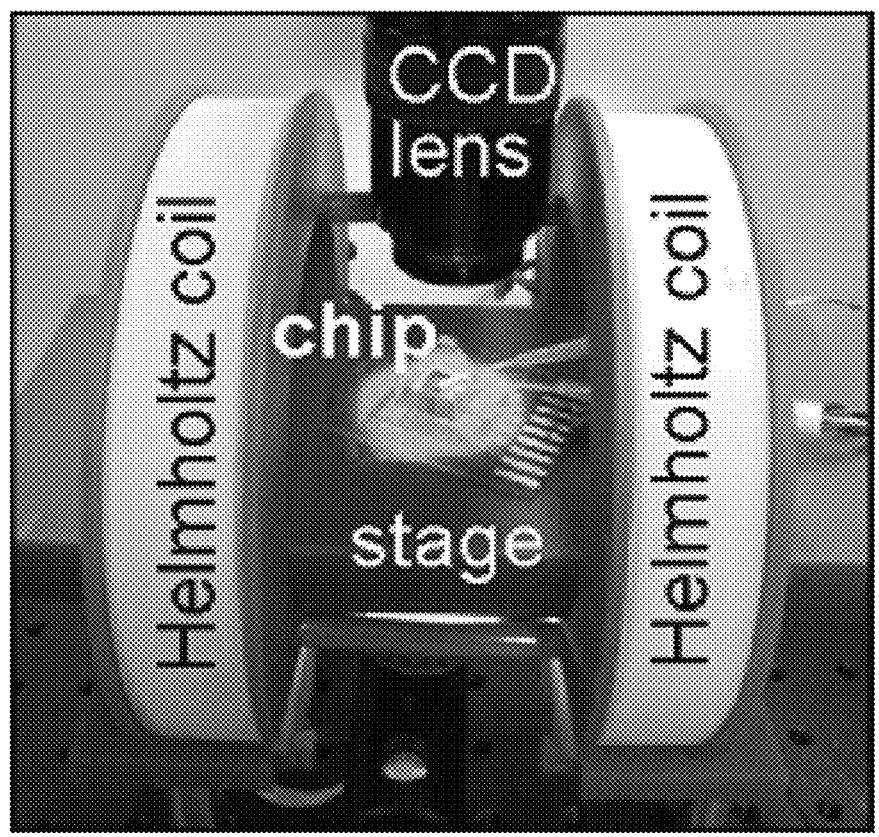
FIG. 8 is a photograph showing a measurement arrangement comprising a microfluidic chip, placed in the center of a Helmholtz coil, and a microscope (CCD lens) placed above the microfluidic chip, in which the arrangement is used to microscopically observe in real-time a process in which the magnetic moment value of superparamagnetic nanoparticle beads in a magnetic fluid is continuously measured when the magnetic fluid flows through microfluidic channels in a microfluidic chip according to an embodiment of the present invention.

To the axis in which current electrodes were connected to both ends of one arm of the sensor, a current source (Keithley 6220) was connected and an electric current of 5 mA was applied, and to the axis in which voltage electrodes were connected to both ends of another arm, a nanovoltmeter (Keithley 2182A) was connected. The change in voltage from the nanovoltmeter was measured in real time using the Labview program (FIG. 8).

2. Formation of Magnetic Fluid Droplet in Channel

In order to allow a magnetic fluid containing $Fe_3O_4$ magnetic nanoparticles (superparamagnetic nanoparticle beads) to flow at a constant rate, a continuous phase fluid consisting of 50% PEG solution and 1% SDS solution was allowed to flow to fill the channel. While microscopically observing the T-shaped channel portion in which the continuous phase fluid and the magnetic fluid meet each other, the air pressure of the magnetic fluid was increased. When the magnetic fluid approached the T-shaped channel portion, the pressure of the magnetic fluid was reduced to a level similar to the air pressure of the continuous phase fluid, and thus the magnetic fluid became an oval droplet. When the pressure of the magnetic fluid was controlled, the length of the droplet-shaped magnetic fluid became longer or shorter. As shown in FIG. 5, when the air pressure of the magnetic fluid was reduced, the size of the magnetic fluid droplet was reduced as shown in FIG. 5(a), and when the air pressure was slightly increased, the size of the droplet was slightly increased as shown in FIG. 5(b). In addition, when the air pressure was further increased, the size of the droplet was further increased as shown in FIG. 5(c).

3. Detection of Magnetic Fluid Droplet

Figure 7:
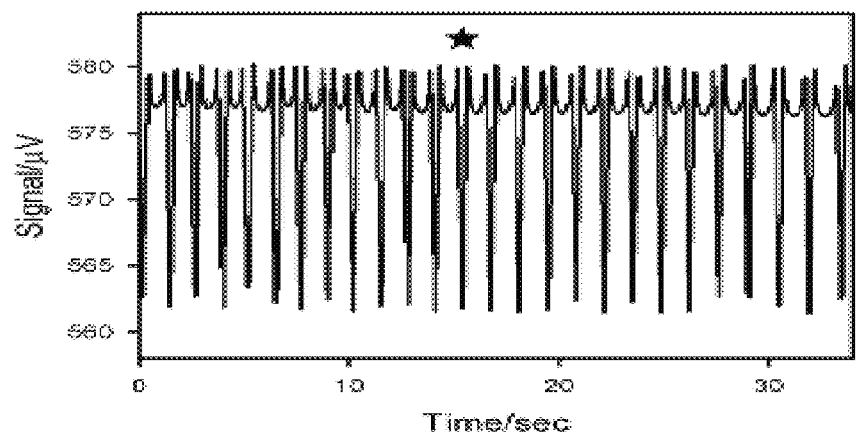
FIG. 7 shows the signal of a magnetic fluid droplet, measured when a superparamagnetic nanoparticle bead droplet passes over a planar Hall resistive sensor according to an embodiment of the present invention, and an enlarged view showing the magnetic fluid that passes over the sensor ((a): the measured magnetic fluid signal of the magnetic fluid, (b): an enlarged view of the measured magnetic sensor signal (★ in FIG. 5(a) of the magnetic fluid; and (c): the magnetic fluid droplet passing over the sensor (time indicated by an arrow in FIG. 5(b))
Figure 7:
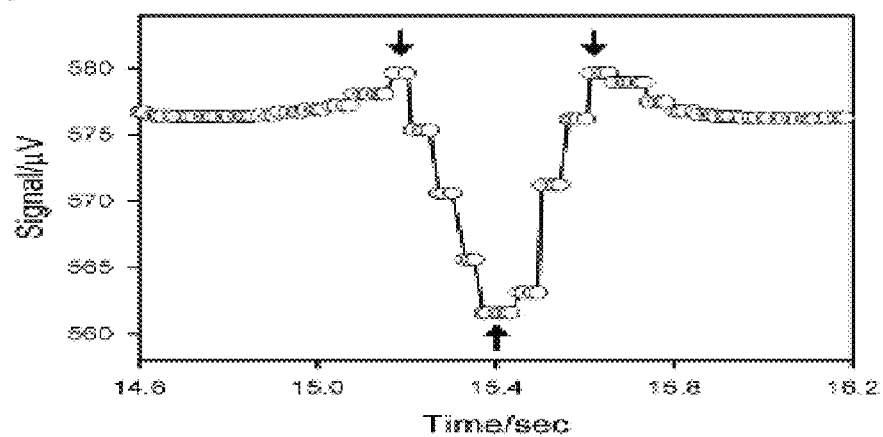
Figure 7:

The magnetic fluid droplet produced in the T-shaped intersection of the microfluidic chip was detected using the planar Hall resistive sensor. The signal shape expected from the simulation results were a low signal between two high signals. The high signals appeared immediately before and after the magnetic fluid passed over the sensor, and were about 3 µV higher than the basic signal. The low signal appeared when the magnetic fluid was present near the sensor, and was about 15 µV lower than the basic signal (FIG. 7).

The obtained magnetic fluid droplet had a length of about 100 µm and a width of 50 µm. The droplet thickness was about 10 µm as determined from the thickness of the microfluidic channel (see FIG. 5(a)). From these values, the volume of the droplet was determined to be about 40 pL. The induced magnetic moment of 50 µL of the magnetic fluid was measured to be about $7\times10^{-3}$ emu at 15 Oe. It can be seen that this value was almost consistent with the value measured by a vibration sample magnetometer as described below (see Comparative Example 1). Based on this value, it can be seen that the magnetic moment of 40 pL of the magnetic fluid droplet is $6\times10^{-9}$ emu. FIG. 7 shows the magnetic sensor signal of the magnetic fluid droplet, measured using the microfluidic chip of the present invention. In FIG. 7, the size of the signal was $14.83\times10$ µV. The minimum size of the sensed signal measured in this system was 0.5 µV, suggesting that a magnetic moment of up to $2\times10^{-10}$ emu can be measured.

4. Calculation of Magnetic Susceptibility $$\chi_V = \frac{1}{S} \frac{\Delta V}{H_{eff}}\bigg|_{H_{app}} \frac{4\pi r^3}{V_{bead}} \quad \text{Equation 2}$$

In the above equation, the sensitivity was $S=2.61\times10^{-6}$ V/Oe, change in output value in the sensor, the change in the sensor output voltage, caused by the stray magnetic field, was $\Delta V=14.83\times10^{-6}$ V (change in signal in FIG. 7(B)), and the volume of the superparamagnetic nanoparticle droplet was $V_{bead}=40$ pL. In addition, the distance (r) between the sensor and the center of the superparamagnetic nanoparticle droplet was r=8.7 µm.

The magnetic susceptibility was calculated by inputting the above values into equation 2, and the calculation result was as follows:

$$\chi_V = \frac{1}{S} \frac{\Delta V}{H_{eff}}\bigg|_{H_{app}} \frac{4\pi r^3}{V_{bead}} \quad \text{Equation 2}$$

Comparative Example 1

Measurement of Magnetic Nanoparticles Using Vibration Sample Magnetometer

In order to examine the magnetic properties of the $Fe_3O_4$ magnetic nanoparticle-containing magnetic fluid used in this experiment and perform a comparison with the signal measured by the sensor, the magnetic properties were measured using a vibration sample magnetometer.

The vibration sample magnetometer is a measurement device that is mostly frequently used to examine the magnetic properties of a sample, and based on a magnetic hysteresis curve obtained by the vibration sample magnetometer, the saturation magnetization, residual magnetization, coercive force, permeability, initial permeability and the like of the sample can be seen. The sample vibrates vertically in a uniform magnetic field at a frequency of about 80 Hz and an amplitude of about 0.1-0.2 mm. A DC signal guided to a measurement coil by the magnetic field of the sample is compared to a signal from a standard magnet and changed to a numerical value proportional to the magnetic moment. The vibration sample magnetometer has advantages in that it has high sensitivity, is easy to operate and is easily used for measurement at room temperature. Because a magnetic fluid diluted in hexadecane is used in place of magnetic nanoparticles during the droplet measurement experiment, the magnetic fluid was placed in the vibration sample magnetometer, and the magnetic properties thereof were measured. 50 µL of the fluid was placed in a glass tube, and the inlet of the glass tube was closed using a glue gun so that the magnetic fluid did not leak. To measure the properties of the magnetic fluid, an experiment was performed under the conditions of an applied field of ±10000 Oe and point 801.

Figure 9:
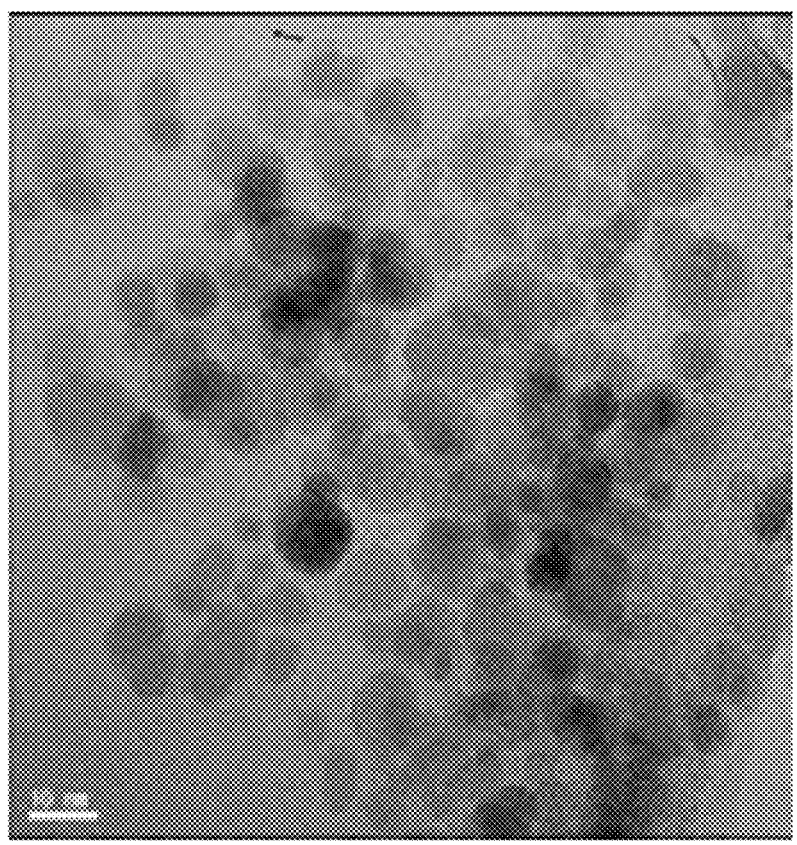
FIG. 9 is a TEM photograph of $Fe_3O_4$ magnetic nanoparticle beads, taken for a TEM sample prepared by drying a magnetic fluid in a TEM grid.

In order to examine the structure of the magnetic nanoparticles, the magnetic nanoparticles were photographed with a transmission electron microscope (TEM) (see FIG. 9). The TEM photography was performed by the Institute for Basic Science (Korea), Gwangju Branch. The magnetic fluid diluted in hexadecane was placed in a TEM grid and dried in an oven to prepare a TEM sample.

Results of Measurement

Figure 10:
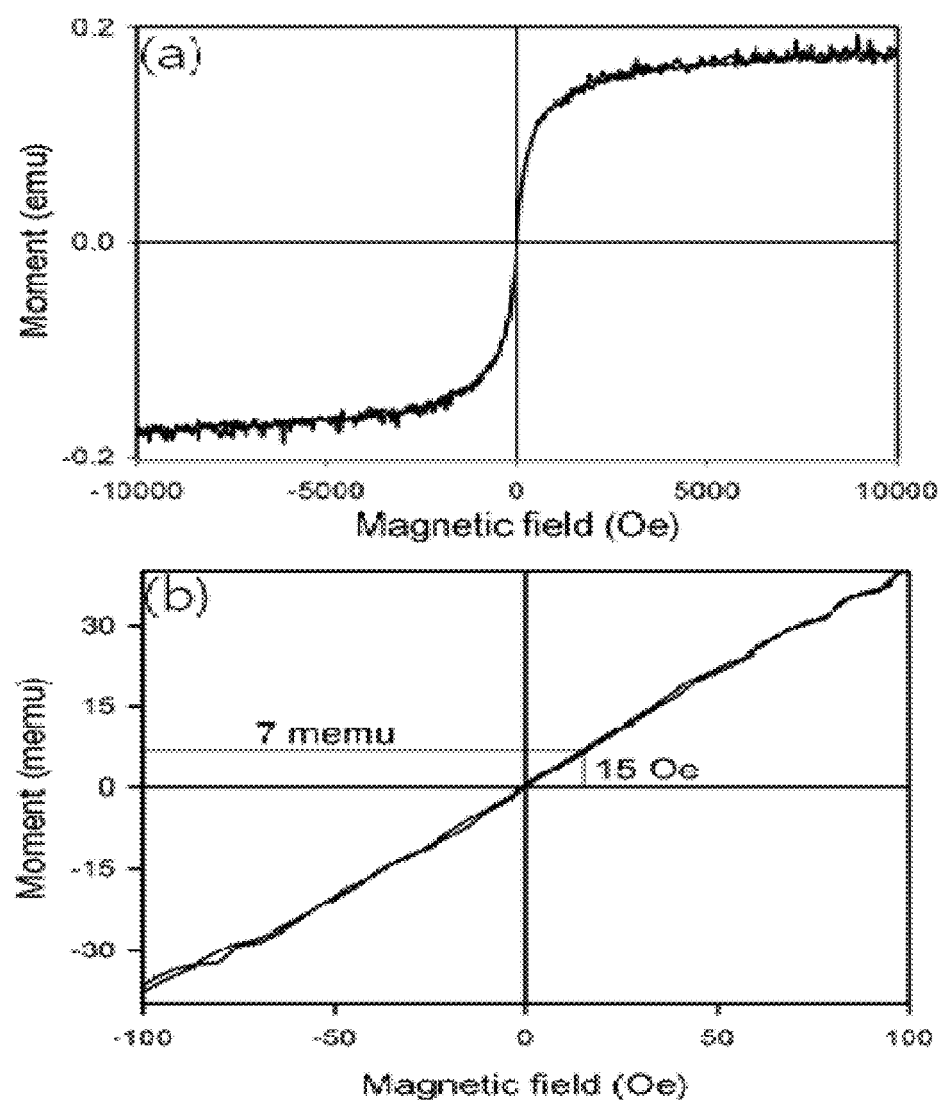
FIG. 10 shows magnetic hysteresis curves of 50 μL of a magnetic fluid, consisting of $Fe_3O_4$ magnetic nanoparticle beads dispersed in hexadecane, at room temperature according to an embodiment of the present invention ((a): a vibration sample magnetometer (VSM) curve in an external magnetic field between −10000 Oe and 10000 Oe, and (b): a vibration sample magnetometer (VSM) curve in an external magnetic field between −100 Oe and 100 Oe)

Generally, the magnetic nanoparticles of a magnetic fluid are synthesized in an organic solvent. Because the magnetic nanoparticles are not easily dispersed in water, they need to be surface-treated so as to be dispersed in water. In the present invention, an organic solvent-based magnetic fluid was used. Specifically, a dilution of the nanoparticles in hexadecane was used, and thus a hexadecane sample was used. A noise having a high amplitude was recorded in the magnetic moment in a high magnetic field, because liquid was used in the measurement employing the vibration sample magnetometer. The magnetic fluid has no residual magnetization at H=0 and is saturated at 3.4 emu/cc, suggesting that it has superparamagnetic properties. The characteristics of the magnetic sensor used in the present invention are exhibited in a low magnetic field of 100 Oe. In order to closely examine the magnetic properties of the magnetic nanoparticles used in this magnetic field, the vibration sample magnetometer curve shown in FIG. 10(a) was enlarged (FIG. 10(b)). It could be seen that the magnetic moment in this magnetic field was linearly proportional to the intensity of the magnetic field and there was no residual magnetization at H=0. In addition, 50 µL of the magnetic nanoparticle liquid used in this experiment was 7 memu at 15 Oe. As shown in the TEM photograph of FIG. 10, the magnetic nanoparticles were spherical nanoparticles having a size of 10-20 nm.

The magnetic susceptibility per volume was calculated using equation 2.

Comparative Example 2

Fabrication 2 of Planar Hall Resistive Sensor

A cross-shaped planar Hall resistive sensor having an arm length of 5 µm and comprising an active junction area having a side length of 3 µm was fabricated in the same manner as described in Example 1.

Comparative Example 3

Fabrication 3 of Planar Hall Resistive Sensor

A cross-shaped planar Hall resistive sensor having an arm length of 3 μm and comprising an active junction area having a side length of 3 μm was fabricated in the same manner as described in Example 1.

Comparative Example 4

Fabrication 4 of Planar Hall Resistive Sensor

A cross-shaped planar Hall resistive sensor having an arm length of 9 μm and comprising an active junction area having a side length of 3 μm was fabricated in the same manner as described in Example 1.

Comparative Example 5

Fabrication 5 of Planar Hall Resistive Sensor

A cross-shaped planar Hall resistive sensor having an arm length of 11 μm and comprising an active junction area having a side length of 3 μm was fabricated in the same manner as described in Example 1.

Comparative Example 6

Fabrication 5 of Planar Hall Resistive Sensor

A cross-shaped planar Hall resistive sensor having an arm length of 13 μm and comprising an active junction area having a side length of 3 μm was fabricated in the same manner as described in Example 1.

Test Example 1

Measurement 1 of Effective Magnetic Field in Cross-Shaped Planar Hall Resistive Sensor According to the Present Invention Using the cross-shaped planar Hall resistive sensors of Example 1 of the present invention and Comparative Example 3, the effective magnetic field in the sensor according to the distance between the sensor surface and the bead was measured, and the results of the measurement are shown in FIG. 5.

Specifically, an external magnetic field having an intensity of 477.48 A·m$^{-1}$ was applied, and the effective magnetic fields in the center and edge of the sensor were measured and averaged.

Referring to FIG. 5, the sensor of Example 1 according to the present invention showed an average effective magnetic field of 548.30 A·m$^{-1}$ when the superparamagnetic bead came into contact with the sensor surface, and showed an average effective magnetic field of about 475.89 A·m$^{-1}$ similar to the intensity of the applied external magnetic field when the distance of the superparamagnetic bead from the sensor was 0.5 μm or more.

Unlike this, the sensor of Comparative Example 3 showed an average effective magnetic field of 700 A·m$^{-1}$ when the superparamagnetic bead came into contact with the sensor surface, and showed an average effective magnetic field similar to the intensity of the external magnetic field when the distance of the superparamagnetic bead from the sensor surface was 2.0 μm or more.

This suggests that the inventive method for measuring magnetic susceptibility can measure the magnetic susceptibility of the superparamagnetic bead by controlling the length of the arm protruding from the active junction area.

Test Example 2

Measurement 2 of Effective Magnetic Field in Cross-Shaped Planar Hall Resistive Sensor According to the Present Invention Using the cross-shaped planar Hall resistive sensors of Example 1 of the present invention and Comparative Examples 2 to 6, the effective magnetic field in the sensor according to the distance between the sensor surface and the bead was measured, and the results of the measurement are shown in FIG. 6.

Specifically, an external magnetic field having an intensity of 477.48 A·m$^{-1}$ was applied, and the effective magnetic fields in the cross-shaped planar Hall resistive sensors having varying arm lengths and comprising an active junction area having a side length of 3 μm were calculated.

Referring to FIG. 6, the sensor of Example 1 according to the present invention showed an average effective magnetic field of 500 A·m$^{-1}$ when the superparamagnetic bead came into contact with the sensor surface, and showed an average effective magnetic field of about 475.89 A·m$^{-1}$ similar to the intensity of the applied external magnetic field when the distance of the superparamagnetic bead from the sensor was 0.5 μm or more.

Unlike this, it can be seen that the sensors of Comparative Examples 3 to 6 showed a very high or low average effective magnetic field compared to the applied external magnetic field when the superparamagnetic bead came into contact with the sensor surface, and showed an average effective magnetic field similar to the intensity of the external magnetic field when the distance of the superparamagnetic bead from the sensor surface was 2.0 μm or more.

This suggests that, according to the inventive method for measuring magnetic susceptibility, when the arm length of the cross-shaped planar Hall resistive sensor is controlled such that the intensity of the effective magnetic field in the sensor can most closely approach the intensity of the applied external magnetic field, the magnetic susceptibility of the superparamagnetic bead can be measured.

Test Example 3

Measurement of Sensing Performance of Cross-Shaped Planar Hall Resistive Sensor According to the Present Invention In order to measure the superparamagnetic bead sensing performance of the cross-shaped planar Hall resistive sensor having a controlled arm length according to the present invention, an electric current of 1 mA was applied, and then the output signal of the sensor according to the intensity of the external magnetic field was measured by the four-point probe method.

Figure 17:
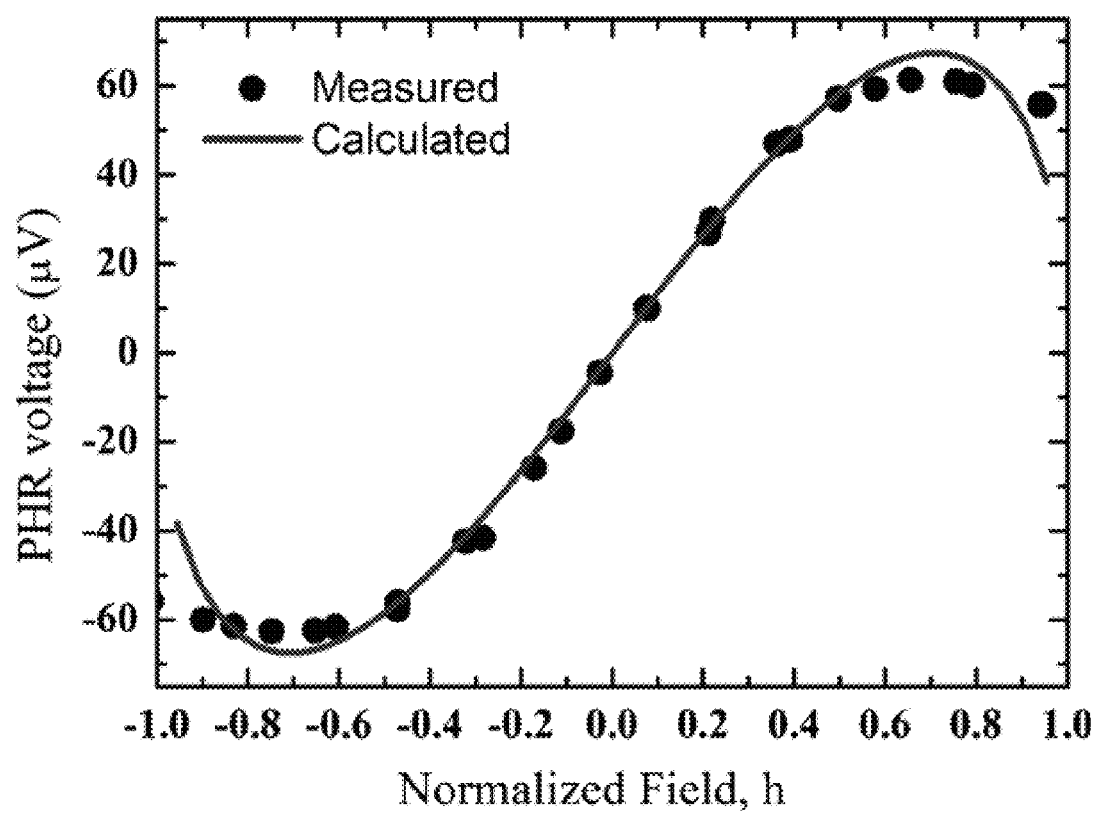
FIG. 17 shows the experimental value and theoretical value of an output signal from a planar Hall resistive sensor of Example 1 of the present invention as a function of the intensity of an external magnetic field.

FIG. 17 shows the output signal of the planar Hall resistive sensor of Example 1 as a function of the intensity of the external magnetic field and shows the measurement value obtained by the above experiment together with the theoretical value calculated using the following equation 4:

$$V(H) = V_o h\sqrt{1-h^2} \text{ for } \sin \Phi \cong \frac{H}{H_{ex}} \equiv h \quad \text{Equation 4}$$

wherein $V_o$ is a constant that varies depending on the material of the sensor, $\Phi$ is the angle between the current flow and the magnetization direction, $H_{ex}$ is a magnetic field caused by an exchange bonding force, H is an externally applied magnetic field, and h is a normalized average magnetic field. In this experiment, $H_{ex}$ was 1.59 kA·m$^{-1}$, and $V_o$ was 120 µV.

Referring to FIG. 17, it can be seen that the sensitivity of the sensor was measured to be 0.075 µV/A·m$^{-1}$ (6.0 µV/Oe) and the measured signal of the sensor was almost consistent with the output single calculated using equation 4.

This suggests that the inventive method for measuring magnetic susceptibility can increase the magnetic field sensitivity of the sensor to enable the magnetic susceptibility of a single bead to be measured.

Test Example 4

Measurement of Magnetic Bead Sensing Properties of Cross-Shaped Planar Hall Resistive Sensor According to the Invention and Measurement of Magnetic Susceptibility In order to test the magnetic bead sensing performance of the cross-shaped planar Hall resistive sensor of Example of the present invention, which has a controlled arm length, the change in voltage in the sensor was measured by performing repeated magnetic bead drop-washing experiments, and the results of the measurement are shown in FIG. 8.

The magnetic bead drop-washing experiment was performed by measuring the change in output between when a superparamagnetic bead (Dynabed®-280) having a diameter of 2.8 µm was placed on the surface of the sensor of Example 1 (drop) and when the bead was removed from the sensor surface (washing), under an external magnetic field of 477.48 A·m$^{-1}$.

Figure 18:
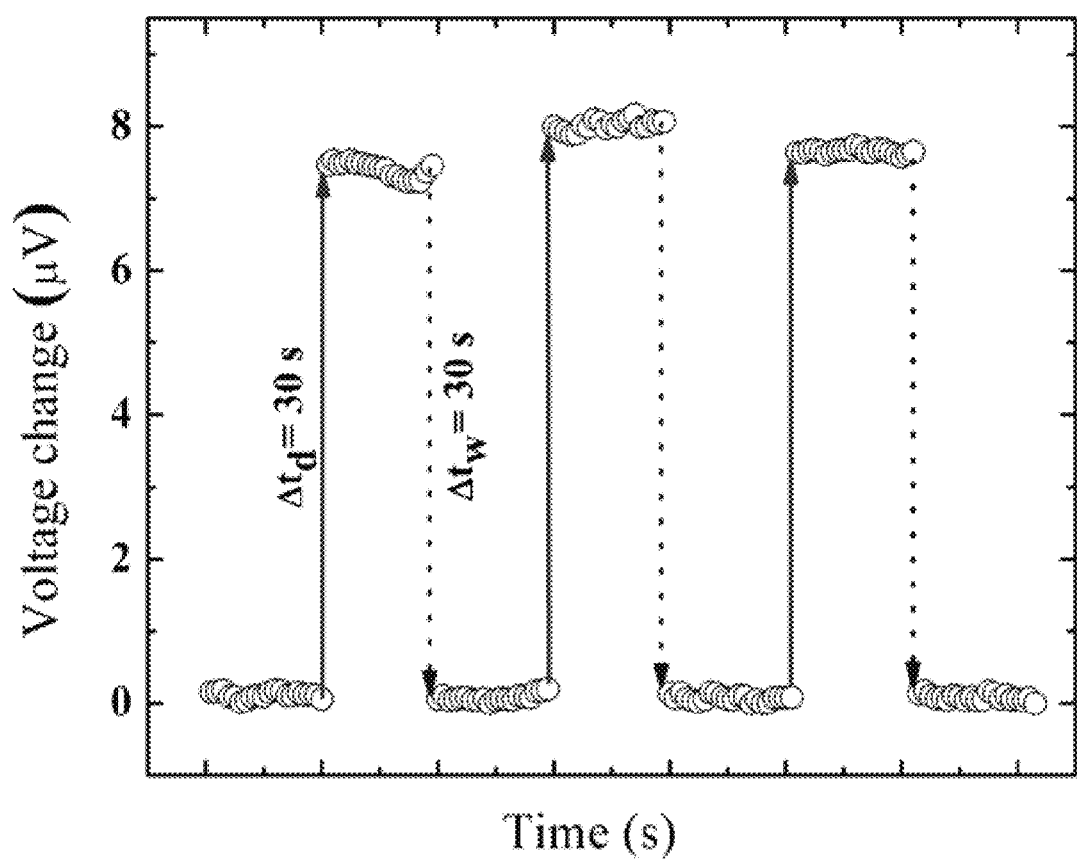
FIG. 18 shows the change in voltage of a planar Hall resistive sensor of Example 1 of the present invention during the repeated bead drop-washing.

Referring to FIG. 18, the change in the average output signal of the sensor by the superparamagnetic bead was measured to be 7.6 µV, and the standard deviation was measured to be 0.26 µV. The deviation was believed to be attributable to the change in the magnetic property of each bead.

This suggests that the inventive method for measuring magnetic susceptibility can measure the magnetic susceptibility of a single superparamagnetic bead, and thus can measure the distribution of the change in the magnetic susceptibility property of a single bead which is industrially produced.

Test Example 5

Measurement of Magnetic Susceptibility of Superparamagnetic Bead by Cross-Shaped Planar Resistive Sensor According to the Present Invention For comparison with the magnetic susceptibility value measured using the cross-shaped planar Hall resistive sensor optimized in Example 1 of the present invention, the magnetic susceptibility of a superparamagnetic bead (Dynabed®-280) having a diameter of 2.8 µm was measured using a superconducting quantum interference device (SQUID; manufactured by Quantum Design). In addition, the measured values were compared with the literature values obtained by measuring the same bead using a vibration sample magnetometer (manufactured by Lake Shore). The results of the measurement are shown in Table 1 below.

TABLE 1

| Measurement method | Magnetic susceptibility ($\chi_v$) |
|---|---|
| Cross-shaped planar Hall resistive sensor (Example 1) | 0.65 |
| superconducting quantum interference device (SQUID) | 0.70 |
| Vibration sample magnetometer (VSM) (1) | 0.75 |
| Vibration sample magnetometer (VSM) (2) | 0.21 |
| Vibration sample magnetometer (VSM) (3) | 0.19 |

As can be seen in Table 1 above, even though the magnetic susceptibility of the same superparamagnetic bead was measured, the magnetic susceptibility of the bead varied depending on the measurement method. Particularly, the measurement method employing the vibration sample magnetometer was used to measure the magnetic susceptibility of the same bead sample, the magnetic susceptibility value of the bead changed in the range of 0.19-0.75 depending on the experimental conditions.

This suggests that the inventive method for measuring magnetic susceptibility can measure the magnetic susceptibility of a single superparamagnetic bead, unlike the prior system for measuring a magnetic material, and thus can be applied to measure the distribution of the change in the magnetic susceptibility.

References for the measurement values obtained by the vibration sample magnetometer (1): G. Fonnum, C. Johansson, A. Molteberg, S. Morup, E. Aksnes, "Characterization of Dynabeads by magnetization measurements and Mossbauer spectroscopy", J. Magn. Magn. Mater. 293 (2005) 41-47, (2): http://wenku.baidu.com/view/c9198d0c4a7302768e9939ea.html, and (3): http://www.invitrogen.co.uk/site/us/en/home/References/protocols/nucleic-acid-purification-and-analysis/mrna-protocols/dynabeads-oligo-dT-25.html)

DESCRIPTION OF REFERENCE NUMBERS

1: SUBSTRATE
2: CURRENT ELECTRODE
3: FIRST ARM
4: VOLTAGE ELECTRODE
5: SECOND ARM
6: ACTIVE JUNCTION AREA
7: MICRO FLUIDIC CHANNEL
10: UNDERLAYER
11: CONTINUOUS PHASE FLUID-MOVING MICROFLUIDIC CHANNEL
12: MAGNETIC FLUID-MOVING MICROFLUIDIC CHANNEL
13: SUPERPARAMAGNETIC NANO BEAD DROPLET-MOVING MICROFLUIDIC CHANNEL
14: INLET FOR INJECTING CONTINUOUS FLUID
15: INLET FOR INJECTING MAGNETIC FLUID
16: OUTLET
20: FIRST FERROMAGNETIC LAYER
30: SPACER LAYER

40: SECOND FERROMAGNETIC LAYER
50: ANTI-FERROMAGNETIC LAYER
60: CAPPING LAYER
200: ACTIVE JUNCTION AREA OF PLANAR HALL RESISTIVE SENSOR AND FIRST, SECOND ARM
300: DEPOSITED STRUCTURE OF PLANAR HALL RESISTIVE SENSOR'S ARM
301: CONTINUOUS FLUID
302: MAGNETIC FLUID
303: SUPERPARAMAGNETIC NANO BEAD DROPLET

What is claimed is:

1. A method for measuring the magnetic susceptibility of a superparamagnetic nanoparticle bead comprises the steps of:
   (1) injecting a continuous phase fluid and a magnetic fluid into a continuous phase fluid-moving microfluidic channel and a magnetic fluid-moving microfluidic channel, respectively, in a microfluidic chip;
   (2) allowing the continuous phase fluid and the magnetic fluid, injected in step (1), to meet each other to form a superparamagnetic nanoparticle bead droplet; and
   (3) measuring the magnetic susceptibility of a superparamagnetic nanoparticle bead present in the droplet when the superparamagnetic nanoparticle bead droplet formed in step (2) passes over an active junction area of a planar Hall resistive sensor,
   wherein the microfluidic chip comprises a planar Hall resistive sensor comprising an active junction area for sensing the superparamagnetic nanoparticle bead and droplet, which protrudes from an underlying substrate and in which a first arm having current electrodes at both ends and a second arm having voltage electrodes at both ends cross each other, wherein the first arm has a controlled length; and microfluidic channels crossing over the active junction area of the planar Hall resistive sensor.

2. The method of claim 1, wherein the continuous phase fluid is a mixed solution of polyethylene glycol and sodium dodecylsulfate.

3. The method of claim 1, wherein the magnetic fluid is a dispersion of the superparamagnetic nanoparticle bead in an organic solvent.

4. The method of claim 1, wherein the continuous phase fluid and the magnetic fluid are capable of controlling the size of the superparamagnetic nanoparticle bead droplet, which is formed at the T-shaped interaction between the microfluidic channels, by controlling their injection pressure.

5. The method of claim 1, wherein the magnetic susceptibility of the superparamagnetic nanoparticle bead droplet is capable of being measured by controlling the length of the first arm of the planar Hall resistive sensor so as to satisfy the condition shown in the following equation 1 when the superparamagnetic nanoparticle bead drop passes over the active junction area of the planar Hall resistive sensor through the intersection of the T-shaped microfluidic channel structure:

$$H_{eff} = H_{app} - H_{stray} \quad \text{Equation 1}$$

wherein $H_{eff}$ is an effective magnetic field in the sensor, $H_{app}$ is an applied external magnetic field, and $H_{stray}$ is a stray magnetic field generated from the magnetized magnetic beads.

6. The method of claim 1, wherein each of the first arm and second arm of the planar Hall resistive sensor is a spin-valve-type sensor thin film structure comprising:
   a underlayer deposited on the underlying substrate;
   a first ferromagnetic layer deposited on the underlayer;
   a spacer layer deposited on the first ferromagnetic layer;
   a second ferromagnetic layer deposited on the spacer layer;
   an anti-ferromagnetic layer deposited on the second ferromagnetic layer; and
   a capping layer deposited on the anti-ferromagnetic layer.

7. The method of claim 6, wherein the underlayer is made of tantalum (Ta) or titanium (Ti); the first layer is made of nickel-iron (NiFe), nickel cobalt (NiCo) or cobalt-iron (CoFe); the spacer layer is made of any one selected from the group consisting of Cu, Ta, rubidium (Ru) and Pd; the second ferromagnetic layer is made of nickel-iron (NiFe), nickel cobalt (NiCo) or cobalt-iron (CoFe); the anti-ferromagnetic layer is made of any one selected from the group consisting of IrMn, NiO, FeMn and PtMn; and the capping layer is made of tantalum (Ta) or titanium (Ti).

8. The method of claim 1, wherein each of the current electrodes at both ends of the first arm and the voltage electrodes at both ends of the second arm of the planar Hall resistive sensor consists of a tantalum (Ta) layer and a layer deposited on the tantalum layer and made of any one selected from the group consisting of Au, Cu and Ag.

9. The method of claim 1, wherein the microfluidic channels have a T-shaped channel structure comprising:
   a continuous phase fluid and a microfluidic channel through which the continuous phase fluid moves;
   a magnetic fluid and a microfluidic channel through which the magnetic fluid moves; and
   a superparamagnetic nanoparticle bead droplet formed at a position at which the two channels meet each other, and a microfluidic channel through which the formed droplet moves.

10. The method of claim 9, wherein the continuous phase fluid is a mixed solution of polyethylene glycol and sodium dodecylsulfate.

11. The method of claim 9, wherein the magnetic fluid is a dispersion of the superparamagnetic nanoparticle bead in an organic solvent.

12. The method of claim 11, wherein the organic solvent is hexadecane.

13. The method of claim 9, wherein the continuous phase fluid and magnetic fluid of the microfluidic channels are capable of controlling the size of the magnetic fluid droplet at the T-shaped intersection by controlling their air pressure.

14. The method of claim 1, wherein the microfluidic channels further comprise: a first inlet port for injecting the continuous phase fluid into the microfluidic channel through which the continuous phase fluid moves; a second inlet port for injecting the magnetic fluid into the microfluidic channel through which the magnetic fluid moves; and an outlet port for discharging the continuous phase fluid and the magnetic fluid droplet from the chip after passage over the active junction area.

* * * * *